(12) United States Patent
Felix et al.

(10) Patent No.: US 9,717,432 B2
(45) Date of Patent: Aug. 1, 2017

(54) EXTENDED WEAR ELECTROCARDIOGRAPHY PATCH USING INTERLACED WIRE ELECTRODES

(71) Applicant: Bardy Diagnostics, Inc., Vashon, WA (US)

(72) Inventors: Jason Felix, Vashon Island, WA (US); Jon Mikalson Bishay, Seattle, WA (US); Gust H. Bardy, Carnation, WA (US)

(73) Assignee: Bardy Diagnostics, Inc., Charlotte, NC (US)

( * ) Notice: Subject to any disclaimer, the term of this patent is extended or adjusted under 35 U.S.C. 154(b) by 57 days.

(21) Appl. No.: 14/463,585

(22) Filed: Aug. 19, 2014

(65) Prior Publication Data

US 2015/0087951 A1  Mar. 26, 2015

Related U.S. Application Data

(63) Continuation-in-part of application No. 14/080,717, filed on Nov. 14, 2013, now Pat. No. 9,545,204.
(Continued)

(51) Int. Cl.
*A61B 5/0408* (2006.01)
*A61B 5/00* (2006.01)

(52) U.S. Cl.
CPC ........ *A61B 5/04085* (2013.01); *A61B 5/0408* (2013.01); *A61B 5/6823* (2013.01);
(Continued)

(58) Field of Classification Search
CPC ... A61B 5/0478; A61B 5/6801; A61B 5/6823; A61B 5/6832–5/6833; A61B 2560/0421;
(Continued)

(56) References Cited

U.S. PATENT DOCUMENTS 3,215,136 A  11/1965  Holter et al.
3,699,948 A  10/1972  Ota et al.
(Continued)

FOREIGN PATENT DOCUMENTS

DE  19955211  5/2001
EP  1859833  11/2007
(Continued)

OTHER PUBLICATIONS

US 6,527,714, 03/2003, Bardy (withdrawn)
(Continued)

*Primary Examiner* — Lee S Cohen
*Assistant Examiner* — Erin M Cardinal
(74) *Attorney, Agent, or Firm* — Patrick J. S. Inouye; Leonid Kisselev; Krista A. Wittman

(57) ABSTRACT

Physiological monitoring can be provided through a wearable monitor that includes a flexible extended wear electrode patch and a removable reusable monitor recorder. A pair of flexile wires is interlaced or sewn into a flexible backing, serving as electrode signal pickup and electrode circuit traces. The wearable monitor sits centrally on the patient's chest along the sternum, which significantly improves the ability to sense cutaneously cardiac electric signals, particularly those generated by the atrium. The electrode patch is shaped to fit comfortably and conformal to the contours of the chest approximately centered on the sternal midline. To counter the dislodgment due to compressional and torsional forces, non-irritating adhesive is provided on the underside, or contact, surface of the electrode patch, but only on the distal and proximal ends. Interlacing the flexile wires into the flexile backing also provides structural support and malleability against compressional, tensile and torsional forces.

20 Claims, 9 Drawing Sheets

Related U.S. Application Data

(60) Provisional application No. 61/882,403, filed on Sep. 25, 2013.

(52) U.S. Cl.
CPC .... *A61B 5/6833* (2013.01); *A61B 2560/0412* (2013.01); *A61B 2560/0443* (2013.01); *A61B 2560/0456* (2013.01); *A61B 2562/164* (2013.01)

(58) Field of Classification Search
CPC ................ A61B 2560/0443–2560/045; A61B 2560/0468; A61B 2562/0209; A61B 2562/125; A61B 5/04087; A61B 5/04085
USPC ............................... 600/382, 391–393, 509
See application file for complete search history.

(56) References Cited

U.S. PATENT DOCUMENTS

| | | | |
|---|---|---|---|
| 3,893,453 A | 7/1975 | Goldberg | |
| 4,123,785 A | 10/1978 | Cherry et al. | |
| 4,328,814 A * | 5/1982 | Arkans | A61B 5/04286 600/393 |
| 4,441,500 A | 4/1984 | Sessions et al. | |
| 4,532,934 A | 8/1985 | Kelen | |
| 4,550,502 A | 11/1985 | Grayzel | |
| 4,580,572 A * | 4/1986 | Granek | A61B 5/04085 600/388 |
| 4,716,903 A | 1/1988 | Hansen | |
| 4,809,705 A | 3/1989 | Ascher | |
| 4,915,656 A | 4/1990 | Alferness | |
| 5,025,794 A | 6/1991 | Albert et al. | |
| 5,168,876 A | 12/1992 | Quedens et al. | |
| 5,215,098 A | 6/1993 | Steinhaus | |
| D341,423 S | 11/1993 | Bible | |
| 5,265,579 A | 11/1993 | Ferrari | |
| 5,341,806 A * | 8/1994 | Gadsby | A61B 5/04085 600/391 |
| 5,355,891 A | 10/1994 | Wateridge et al. | |
| 5,365,934 A | 11/1994 | Leon et al. | |
| 5,392,784 A | 2/1995 | Gudaitis | |
| D357,069 S | 4/1995 | Plahn et al. | |
| 5,402,780 A | 4/1995 | Faasse, Jr. | |
| 5,402,884 A | 4/1995 | Gilman et al. | |
| 5,450,845 A * | 9/1995 | Axelgaard | A61B 5/0408 600/382 |
| 5,458,141 A | 10/1995 | Neil | |
| 5,473,537 A | 12/1995 | Glazer et al. | |
| 5,483,969 A | 1/1996 | Testerman et al. | |
| 5,540,733 A | 7/1996 | Testerman et al. | |
| 5,546,952 A | 8/1996 | Erickson | |
| 5,549,655 A | 8/1996 | Erickson | |
| 5,579,919 A | 12/1996 | Gilman et al. | |
| 5,582,181 A | 12/1996 | Ruess | |
| D377,983 S | 2/1997 | Sabri et al. | |
| 5,601,089 A | 2/1997 | Bledsoe et al. | |
| 5,623,935 A | 4/1997 | Faisandier | |
| 5,682,901 A | 11/1997 | Kamen | |
| 5,697,955 A | 12/1997 | Stolte | |
| 5,749,902 A | 5/1998 | Olsen et al. | |
| 5,817,151 A | 10/1998 | Olsen et al. | |
| 5,819,741 A | 10/1998 | Karlsson et al. | |
| 5,850,920 A | 12/1998 | Gilman et al. | |
| D407,159 S | 3/1999 | Roberg | |
| 5,876,351 A | 3/1999 | Rohde | |
| 5,906,583 A | 5/1999 | Rogel | |
| 5,951,598 A | 9/1999 | Bishay et al. | |
| 5,957,857 A | 9/1999 | Hartley | |
| 5,984,102 A | 11/1999 | Tay | |
| 6,032,064 A * | 2/2000 | Devlin | A61B 5/04004 600/372 |
| 6,038,469 A | 3/2000 | Karlsson et al. | |
| 6,101,413 A | 8/2000 | Olson et al. | |
| 6,115,638 A | 9/2000 | Groenke | |
| 6,117,077 A | 9/2000 | Del Mar et al. | |
| 6,134,479 A | 10/2000 | Brewer et al. | |
| 6,148,233 A | 11/2000 | Owen et al. | |
| 6,149,602 A | 11/2000 | Arcelus | |
| 6,149,781 A | 11/2000 | Forand | |
| 6,188,407 B1 | 2/2001 | Smith et al. | |
| D443,063 S * | 5/2001 | Pisani | D24/187 |
| 6,245,025 B1 | 6/2001 | Torok et al. | |
| 6,246,330 B1 | 6/2001 | Nielsen | |
| D445,507 S * | 7/2001 | Pisani | D24/187 |
| 6,269,267 B1 | 7/2001 | Bardy et al. | |
| 6,272,385 B1 | 8/2001 | Bishay et al. | |
| 6,298,255 B1 * | 10/2001 | Cordero | A61B 5/04085 600/372 |
| 6,301,502 B1 | 10/2001 | Owen et al. | |
| 6,304,773 B1 | 10/2001 | Taylor et al. | |
| 6,304,780 B1 | 10/2001 | Owen et al. | |
| 6,304,783 B1 | 10/2001 | Lyster et al. | |
| 6,374,138 B1 | 4/2002 | Owen et al. | |
| 6,416,471 B1 | 7/2002 | Kumar et al. | |
| 6,418,342 B1 | 7/2002 | Owen et al. | |
| 6,424,860 B1 | 7/2002 | Karlsson et al. | |
| 6,427,083 B1 | 7/2002 | Owen et al. | |
| 6,456,872 B1 | 9/2002 | Faisandier | |
| 6,463,320 B1 | 10/2002 | Xue et al. | |
| 6,546,285 B1 | 4/2003 | Owen et al. | |
| 6,605,046 B1 | 8/2003 | Del Mar | |
| 6,607,485 B2 | 8/2003 | Bardy | |
| 6,611,705 B2 | 8/2003 | Hopman et al. | |
| 6,671,545 B2 | 12/2003 | Fincke | |
| 6,671,547 B2 | 12/2003 | Lyster et al. | |
| 6,694,186 B2 | 2/2004 | Bardy | |
| 6,704,595 B2 | 3/2004 | Bardy | |
| 6,705,991 B2 | 3/2004 | Bardy | |
| 6,719,701 B2 | 4/2004 | Lade | |
| 6,754,523 B2 | 6/2004 | Toole | |
| 6,782,293 B2 | 8/2004 | Dupelle et al. | |
| 6,856,832 B1 | 2/2005 | Matsumura et al. | |
| 6,860,897 B2 | 3/2005 | Bardy | |
| 6,866,629 B2 | 3/2005 | Bardy | |
| 6,887,201 B2 | 5/2005 | Bardy | |
| 6,893,397 B2 | 5/2005 | Bardy | |
| 6,904,312 B2 | 6/2005 | Bardy | |
| 6,908,431 B2 | 6/2005 | Bardy | |
| 6,913,577 B2 | 7/2005 | Bardy | |
| 6,944,498 B2 | 9/2005 | Owen et al. | |
| 6,960,167 B2 | 11/2005 | Bardy | |
| 6,970,731 B1 * | 11/2005 | Jayaraman | A61B 5/0008 600/388 |
| 6,978,169 B1 | 12/2005 | Guerra | |
| 6,993,377 B2 | 1/2006 | Flick et al. | |
| 7,020,508 B2 | 3/2006 | Stivoric et al. | |
| 7,027,864 B2 | 4/2006 | Snyder et al. | |
| 7,065,401 B2 | 6/2006 | Worden | |
| 7,085,601 B1 | 8/2006 | Bardy et al. | |
| 7,104,955 B2 | 9/2006 | Bardy | |
| 7,134,996 B2 | 11/2006 | Bardy | |
| 7,137,389 B2 | 11/2006 | Berthon-Jones | |
| 7,147,600 B2 | 12/2006 | Bardy | |
| 7,215,991 B2 | 5/2007 | Besson et al. | |
| 7,248,916 B2 | 7/2007 | Bardy | |
| 7,257,438 B2 | 8/2007 | Kinast | |
| 7,277,752 B2 | 10/2007 | Matos | |
| D558,882 S | 1/2008 | Brady | |
| 7,328,061 B2 | 2/2008 | Rowlandson et al. | |
| 7,412,395 B2 | 8/2008 | Rowlandson et al. | |
| 7,429,938 B1 | 9/2008 | Comdorf | |
| 7,552,031 B2 * | 6/2009 | Vock | A43B 3/0005 340/539.13 |
| D606,656 S | 12/2009 | Kobayashi et al. | |
| 7,706,870 B2 | 4/2010 | Shieh et al. | |
| 7,756,721 B1 | 7/2010 | Falchuk et al. | |
| 7,787,943 B2 | 8/2010 | McDonough | |
| 7,874,993 B2 | 1/2011 | Bardy | |
| 7,881,785 B2 | 2/2011 | Nassif et al. | |
| D639,437 S | 6/2011 | Bishay et al. | |
| 7,959,574 B2 | 6/2011 | Bardy | |
| 8,116,841 B2 | 2/2012 | Bly et al. | |

(56) References Cited

U.S. PATENT DOCUMENTS

| | | | |
|---|---|---|---|
| 8,172,761 B1 | 5/2012 | Rulkov et al. | |
| 8,180,425 B2 * | 5/2012 | Selvitelli | A61B 5/04085 |
| | | | 600/382 |
| 8,200,320 B2 | 6/2012 | Kovacs | |
| 8,231,539 B2 | 7/2012 | Bardy | |
| 8,231,540 B2 | 7/2012 | Bardy | |
| 8,239,012 B2 | 8/2012 | Felix et al. | |
| 8,249,686 B2 | 8/2012 | Libbus et al. | |
| 8,260,414 B2 | 9/2012 | Nassif et al. | |
| 8,266,008 B1 | 9/2012 | Siegal et al. | |
| 8,277,378 B2 | 10/2012 | Bardy | |
| 8,285,356 B2 | 10/2012 | Bly et al. | |
| 8,285,370 B2 | 10/2012 | Felix et al. | |
| 8,308,650 B2 | 11/2012 | Bardy | |
| 8,366,629 B2 | 2/2013 | Bardy | |
| 8,374,688 B2 | 2/2013 | Libbus et al. | |
| 8,412,317 B2 | 4/2013 | Mazar | |
| 8,460,189 B2 | 6/2013 | Libbus et al. | |
| 8,473,047 B2 | 6/2013 | Chakravarthy et al. | |
| 8,478,418 B2 | 7/2013 | Fahey | |
| 8,554,311 B2 | 10/2013 | Warner et al. | |
| 8,591,430 B2 | 11/2013 | Amurthur et al. | |
| 8,594,763 B1 | 11/2013 | Bibian et al. | |
| 8,600,486 B2 | 12/2013 | Kaib et al. | |
| 8,613,708 B2 | 12/2013 | Bishay et al. | |
| 8,613,709 B2 | 12/2013 | Bishay et al. | |
| 8,620,418 B1 | 12/2013 | Kuppuraj et al. | |
| 8,626,277 B2 | 1/2014 | Felix et al. | |
| 8,684,925 B2 | 4/2014 | Manicka et al. | |
| 8,688,190 B2 | 4/2014 | Libbus et al. | |
| 8,718,752 B2 | 5/2014 | Libbus et al. | |
| 8,744,561 B2 | 6/2014 | Fahey | |
| 8,774,932 B2 | 7/2014 | Fahey | |
| 8,790,257 B2 | 7/2014 | Libbus et al. | |
| 8,790,259 B2 | 7/2014 | Katra et al. | |
| 8,795,174 B2 | 8/2014 | Manicka et al. | |
| 8,798,729 B2 | 8/2014 | Kaib et al. | |
| 8,798,734 B2 | 8/2014 | Kuppuraj et al. | |
| 8,818,478 B2 | 8/2014 | Scheffler et al. | |
| 8,818,481 B2 | 8/2014 | Bly et al. | |
| 8,823,490 B2 | 9/2014 | Libbus et al. | |
| 8,938,287 B2 | 1/2015 | Felix et al. | |
| 8,965,492 B2 | 2/2015 | Baker et al. | |
| 9,066,664 B2 | 6/2015 | Karjalainen | |
| 9,155,484 B2 | 10/2015 | Baker et al. | |
| 9,204,813 B2 | 12/2015 | Kaib et al. | |
| 9,277,864 B2 | 3/2016 | Yang et al. | |
| 9,339,202 B2 | 5/2016 | Brockway et al. | |
| 2002/0013538 A1 | 1/2002 | Teller | |
| 2002/0013717 A1 | 1/2002 | Ando et al. | |
| 2002/0103422 A1 | 8/2002 | Harder et al. | |
| 2002/0120310 A1 | 8/2002 | Linden et al. | |
| 2002/0184055 A1 | 12/2002 | Naghavi et al. | |
| 2002/0193668 A1 | 12/2002 | Munneke | |
| 2003/0004547 A1 | 1/2003 | Owen et al. | |
| 2003/0073916 A1 | 4/2003 | Yonce | |
| 2003/0083559 A1 | 5/2003 | Thompson | |
| 2003/0097078 A1 | 5/2003 | Maeda | |
| 2003/0139785 A1 | 7/2003 | Riff et al. | |
| 2003/0176802 A1 | 9/2003 | Galen et al. | |
| 2004/0008123 A1 | 1/2004 | Carrender | |
| 2004/0019288 A1 | 1/2004 | Kinast | |
| 2004/0034284 A1 | 2/2004 | Aversano et al. | |
| 2004/0049132 A1 | 3/2004 | Barron et al. | |
| 2004/0087836 A1 | 5/2004 | Green et al. | |
| 2004/0093192 A1 | 5/2004 | Hasson et al. | |
| 2004/0148194 A1 | 7/2004 | Wellons et al. | |
| 2004/0207530 A1 | 10/2004 | Nielsen | |
| 2004/0236202 A1 * | 11/2004 | Burton | A61B 5/0536 |
| | | | 600/384 |
| 2004/0243435 A1 | 12/2004 | Williams | |
| 2004/0256453 A1 | 12/2004 | Lammle | |
| 2004/0260188 A1 | 12/2004 | Syed et al. | |
| 2004/0260192 A1 | 12/2004 | Yamamoto | |
| 2005/0096717 A1 | 5/2005 | Bishay et al. | |
| 2005/0108055 A1 | 5/2005 | Ott et al. | |
| 2005/0154267 A1 | 7/2005 | Bardy | |
| 2005/0182308 A1 | 8/2005 | Bardy | |
| 2005/0182309 A1 | 8/2005 | Bardy | |
| 2005/0215918 A1 * | 9/2005 | Frantz | A61B 5/0537 |
| | | | 600/547 |
| 2005/0222513 A1 | 10/2005 | Hadley et al. | |
| 2005/0228243 A1 | 10/2005 | Bardy | |
| 2005/0245839 A1 | 11/2005 | Stivoric et al. | |
| 2006/0025696 A1 | 2/2006 | Kurzweil et al. | |
| 2006/0025824 A1 | 2/2006 | Freeman et al. | |
| 2006/0030767 A1 | 2/2006 | Lang et al. | |
| 2006/0041201 A1 | 2/2006 | Behbehani et al. | |
| 2006/0122469 A1 | 6/2006 | Martel | |
| 2006/0124193 A1 | 6/2006 | Orr et al. | |
| 2006/0224072 A1 | 10/2006 | Shennib | |
| 2006/0235320 A1 | 10/2006 | Tan et al. | |
| 2006/0253006 A1 | 11/2006 | Bardy | |
| 2006/0264730 A1 | 11/2006 | Stivoric et al. | |
| 2006/0264767 A1 | 11/2006 | Shennib | |
| 2007/0003115 A1 | 1/2007 | Patton et al. | |
| 2007/0038057 A1 * | 2/2007 | Nam | A61B 5/6805 |
| | | | 600/388 |
| 2007/0050209 A1 | 3/2007 | Yered | |
| 2007/0078324 A1 | 4/2007 | Wijisiriwardana | |
| 2007/0093719 A1 | 4/2007 | Nichols, Jr. et al. | |
| 2007/0100248 A1 | 5/2007 | Van Dam et al. | |
| 2007/0100667 A1 | 5/2007 | Bardy | |
| 2007/0123801 A1 | 5/2007 | Goldberger et al. | |
| 2007/0136091 A1 | 6/2007 | McTaggart | |
| 2007/0179357 A1 | 8/2007 | Bardy | |
| 2007/0185390 A1 | 8/2007 | Perkins et al. | |
| 2007/0203415 A1 | 8/2007 | Bardy | |
| 2007/0203423 A1 | 8/2007 | Bardy | |
| 2007/0208232 A1 | 9/2007 | Kovacs | |
| 2007/0208233 A1 | 9/2007 | Kovacs | |
| 2007/0208266 A1 | 9/2007 | Hadley | |
| 2007/0225611 A1 | 9/2007 | Kumar et al. | |
| 2007/0244405 A1 | 10/2007 | Xue et al. | |
| 2007/0249946 A1 | 10/2007 | Kumar et al. | |
| 2007/0255153 A1 | 11/2007 | Kumar et al. | |
| 2007/0265510 A1 | 11/2007 | Bardy | |
| 2007/0276270 A1 | 11/2007 | Tran | |
| 2007/0276275 A1 | 11/2007 | Proctor et al. | |
| 2007/0293738 A1 | 12/2007 | Bardy | |
| 2007/0293739 A1 | 12/2007 | Bardy | |
| 2007/0293740 A1 | 12/2007 | Bardy | |
| 2007/0293741 A1 | 12/2007 | Bardy | |
| 2007/0293772 A1 | 12/2007 | Bardy | |
| 2007/0299325 A1 | 12/2007 | Farrell et al. | |
| 2007/0299617 A1 | 12/2007 | Willis | |
| 2008/0051668 A1 | 2/2008 | Bardy | |
| 2008/0058661 A1 | 3/2008 | Bardy | |
| 2008/0091097 A1 * | 4/2008 | Linti | A41D 13/1281 |
| | | | 600/389 |
| 2008/0108890 A1 * | 5/2008 | Teng | A61B 5/04087 |
| | | | 600/372 |
| 2008/0139953 A1 * | 6/2008 | Baker | A61B 5/0006 |
| | | | 600/509 |
| 2008/0143080 A1 | 6/2008 | Burr | |
| 2008/0177168 A1 * | 7/2008 | Callahan | A61B 5/04085 |
| | | | 600/382 |
| 2008/0194927 A1 | 8/2008 | KenKnight et al. | |
| 2008/0208009 A1 | 8/2008 | Shklarski | |
| 2008/0208014 A1 | 8/2008 | KenKnight et al. | |
| 2008/0284599 A1 | 11/2008 | Zdeblick et al. | |
| 2008/0288026 A1 * | 11/2008 | Cross | A61B 5/0408 |
| | | | 607/60 |
| 2008/0306359 A1 | 12/2008 | Zdeblick et al. | |
| 2009/0054952 A1 | 2/2009 | Glukhovsky et al. | |
| 2009/0062897 A1 * | 3/2009 | Axelgaard | A61N 1/0452 |
| | | | 607/152 |
| 2009/0069867 A1 | 3/2009 | KenKnight et al. | |
| 2009/0073991 A1 | 3/2009 | Landrum et al. | |
| 2009/0076336 A1 | 3/2009 | Mazar et al. | |
| 2009/0076341 A1 | 3/2009 | James et al. | |
| 2009/0076342 A1 | 3/2009 | Amurthur et al. | |
| 2009/0076343 A1 | 3/2009 | James et al. | |

(56) References Cited

U.S. PATENT DOCUMENTS

| | | |
|---|---|---|
| 2009/0076346 A1 | 3/2009 | James et al. |
| 2009/0076349 A1 | 3/2009 | Libbus et al. |
| 2009/0076397 A1 | 3/2009 | Libbus et al. |
| 2009/0076401 A1 | 3/2009 | Mazar et al. |
| 2009/0076559 A1 | 3/2009 | Libbus et al. |
| 2009/0088652 A1* | 4/2009 | Tremblay ............ A41D 13/1281 600/388 |
| 2009/0112116 A1 | 4/2009 | Lee et al. |
| 2009/0131759 A1 | 5/2009 | Sims et al. |
| 2009/0216132 A1 | 8/2009 | Orbach |
| 2009/0270708 A1 | 10/2009 | Shen et al. |
| 2009/0270747 A1 | 10/2009 | Van Dam et al. |
| 2009/0292194 A1 | 11/2009 | Libbus et al. |
| 2010/0007413 A1 | 1/2010 | Herleikson |
| 2010/0022897 A1 | 1/2010 | Parker et al. |
| 2010/0056881 A1 | 3/2010 | Libbus et al. |
| 2010/0081913 A1 | 4/2010 | Cross et al. |
| 2010/0185063 A1 | 7/2010 | Bardy |
| 2010/0185076 A1 | 7/2010 | Jeong et al. |
| 2010/0191154 A1 | 7/2010 | Berger et al. |
| 2010/0191310 A1 | 7/2010 | Bly |
| 2010/0234715 A1 | 9/2010 | Shin et al. |
| 2010/0234716 A1 | 9/2010 | Engel |
| 2010/0280366 A1 | 11/2010 | Arne et al. |
| 2010/0324384 A1 | 12/2010 | Moon et al. |
| 2011/0021937 A1 | 1/2011 | Hugh et al. |
| 2011/0054286 A1 | 3/2011 | Crosby et al. |
| 2011/0066041 A1 | 3/2011 | Pandia et al. |
| 2011/0077497 A1* | 3/2011 | Oster .................. A61B 5/0002 600/372 |
| 2011/0144470 A1 | 6/2011 | Mazar et al. |
| 2011/0160548 A1 | 6/2011 | Forster et al. |
| 2011/0224564 A1 | 9/2011 | Moon et al. |
| 2011/0237924 A1 | 9/2011 | McGusty et al. |
| 2011/0245699 A1 | 10/2011 | Snell et al. |
| 2011/0245711 A1 | 10/2011 | Katra et al. |
| 2012/0003933 A1 | 1/2012 | Baker et al. |
| 2012/0029306 A1 | 2/2012 | Paquet et al. |
| 2012/0029315 A1 | 2/2012 | Raptis et al. |
| 2012/0029316 A1 | 2/2012 | Raptis et al. |
| 2012/0035432 A1 | 2/2012 | Katra et al. |
| 2012/0088998 A1 | 4/2012 | Bardy et al. |
| 2012/0088999 A1 | 4/2012 | Bishay et al. |
| 2012/0089000 A1 | 4/2012 | Bishay et al. |
| 2012/0089001 A1 | 4/2012 | Bishay et al. |
| 2012/0089037 A1 | 4/2012 | Bishay et al. |
| 2012/0089412 A1 | 4/2012 | Bardy et al. |
| 2012/0089417 A1 | 4/2012 | Bardy et al. |
| 2012/0095352 A1 | 4/2012 | Tran |
| 2012/0101358 A1 | 4/2012 | Boettcher et al. |
| 2012/0101396 A1 | 4/2012 | Solosko et al. |
| 2012/0165645 A1 | 6/2012 | Russel et al. |
| 2012/0172695 A1 | 7/2012 | Ko et al. |
| 2012/0302906 A1 | 11/2012 | Felix et al. |
| 2012/0323132 A1 | 12/2012 | Warner et al. |
| 2012/0330126 A1 | 12/2012 | Hoppe et al. |
| 2013/0041272 A1 | 2/2013 | Guillen Arredondo et al. |
| 2013/0077263 A1 | 3/2013 | Oleson et al. |
| 2013/0079611 A1 | 3/2013 | Besko |
| 2013/0085403 A1 | 4/2013 | Gunderson et al. |
| 2013/0096395 A1 | 4/2013 | Katra et al. |
| 2013/0116533 A1 | 5/2013 | Lian et al. |
| 2013/0123651 A1 | 5/2013 | Bardy |
| 2013/0158361 A1 | 6/2013 | Bardy |
| 2013/0225963 A1 | 8/2013 | Kodandaramaiah et al. |
| 2013/0225966 A1 | 8/2013 | Macia Barber et al. |
| 2013/0243105 A1 | 9/2013 | Lei et al. |
| 2013/0274584 A1 | 10/2013 | Finlay et al. |
| 2013/0275158 A1 | 10/2013 | Fahey |
| 2013/0324809 A1 | 12/2013 | Lisogurski et al. |
| 2013/0324855 A1 | 12/2013 | Lisogurski et al. |
| 2013/0324856 A1 | 12/2013 | Lisogurski et al. |
| 2013/0325359 A1 | 12/2013 | Jarverud et al. |
| 2013/0331665 A1 | 12/2013 | Libbus et al. |
| 2013/0338448 A1 | 12/2013 | Libbus et al. |
| 2013/0338472 A1 | 12/2013 | Macia Barber et al. |
| 2014/0012154 A1 | 1/2014 | Mazar et al. |
| 2014/0140359 A1 | 5/2014 | Kalevo et al. |
| 2014/0189928 A1 | 7/2014 | Oleson et al. |
| 2014/0206977 A1 | 7/2014 | Bahney et al. |
| 2014/0215246 A1 | 7/2014 | Lee et al. |
| 2014/0358193 A1 | 12/2014 | Lyons et al. |
| 2015/0048836 A1 | 2/2015 | Guthrie et al. |
| 2015/0065842 A1 | 3/2015 | Lee et al. |
| 2015/0082623 A1* | 3/2015 | Felix .................. A61B 5/04087 29/825 |
| 2015/0165211 A1 | 6/2015 | Navqi et al. |
| 2015/0257670 A1 | 9/2015 | Ortega et al. |
| 2015/0359489 A1 | 12/2015 | Baudenbacher et al. |
| 2016/0217691 A1 | 7/2016 | Kadobayashi et al. |

FOREIGN PATENT DOCUMENTS

| | | |
|---|---|---|
| EP | 2438851 | 4/2012 |
| EP | 2438852 | 4/2012 |
| EP | 2465415 | 6/2012 |
| EP | 2589333 | 5/2013 |
| JP | H06319711 | 11/1994 |
| JP | 2004129788 | 4/2004 |
| WO | 0078213 | 12/2000 |
| WO | 03032192 | 4/2003 |
| WO | 2006009767 | 1/2006 |
| WO | 2006014806 | 2/2006 |
| WO | 2007066270 | 6/2007 |
| WO | 2007092543 | 8/2007 |
| WO | 2008010216 | 1/2008 |
| WO | 2008057884 | 5/2008 |
| WO | 2009036306 | 3/2009 |
| WO | 2009036313 | 3/2009 |
| WO | 2009036327 | 3/2009 |
| WO | 2009112976 | 9/2009 |
| WO | 2009112978 | 9/2009 |
| WO | 2009112979 | 9/2009 |
| WO | 2009142975 | 11/2009 |
| WO | 2010066507 | 6/2010 |
| WO | 2010105045 | 9/2010 |
| WO | 2011047207 | 4/2011 |
| WO | 2012140559 | 10/2012 |
| WO | 2012146957 | 11/2012 |

OTHER PUBLICATIONS 15 of the Hottest Wearable Gadgets, URL <http://thehottestgadgets.com/2008/09/the-15-hottest-wearable-gadgets-001253> (Web page cached on Sep. 27, 2008).

Alivecor's Heart Monitor for iPhone Receives FDA Clearance, URL <http://www.businesswire.com/news/home/20121203005545/en/AliveCor%E2%80%99s-Heart-Monitor-iPhone-Receives-FDA-Clearance#.U7rtq7FVTyF> (Dec. 3, 2012).

Bharadwaj et al., Techniques for Accurate ECG signal processing, EE Times, URL <www.eetimes.com/document.asp?doc_id=1278571> (Feb. 14, 2011).

Chen et al., "Monitoring Body Temperature of Newborn Infants at Neonatal Intensive Care Units Using Wearable Sensors," BodyNets 2010, Corfu Island, Greece. (Sep. 10, 2010).

Epstein, Andrew E. et al.; ACC/AHA/HRS 2008 Guidelines for Device-Based Therapy of Cardiac Rhythm Abnormalities. J. Am. Coll. Cardiol. 2008; 51; el-e62, 66 Pgs.

Fitbit automatically tracks your fitness and sleep, URL <http://www.fitbit.com/> (Web page cached on Sep. 10, 2008).

Smith, Kevin, "Jawbone up VS. Fitbit Flex: Which Is the Best Fitness Band?" URL <http://www.businessinsider.com/fitbit-flex-vs-jawbone-up-2013-5?op=1> (Jun. 1, 2013).

Kligfield, Paul et al., Recommendations for the Standardization and Interpretation of the Electrocardiogram: Part I. J.Am.Coll. Cardiol; 2007; 49; 1109-27, 75 Pgs.

Lauren Gravitz, "When Your Diet Needs a Band-Aid,"Technology Review, MIT. (May 1, 2009).

Lieberman, Jonathan, "How Telemedicine Is Aiding Prompt ECG Diagnosis in Primary Care," British Journal of Community Nursing,

(56) References Cited

OTHER PUBLICATIONS vol. 13, No. 3, Mar. 1, 2008 (Mar. 1, 2008), pp. 123-126, XP009155082, ISSN: 1462-4753.
McManus et al., "A Novel Application for the Detection of an Irregular Pulse using an iPhone 4S in Patients with Atrial Fibrillation," vol. 10(3), pp. 315-319 (Mar. 2013).
Nike+ Fuel Band, URL <http://www.nike.com/us/en_us/c/nikeplus-fuelband> (Web page cached on Jan. 11, 2013).
P. Libby et al.,"Braunwald's Heart Disease—A Textbook of Cardiovascular Medicine," Chs. 11, pp. 125-148 and 12, pp. 149-193 (8th ed. 2008), American Heart Association.
Initial hands-on with Polar Loop activity tracker, URL <http://www.dcrainmaker.com/2013/09/polar-loop-firstlook.html> (Sep. 17, 2013).
Sittig et al., "A Computer-Based Outpatient Clinical Referral System," International Journal of Medical Informatics, Shannon, IR, vol. 55, No. 2, Aug. 1, 1999, pp. 149-158, XO004262434, ISSN: 1386-5056(99)00027-1.
Sleepview, URL <http://www.clevemed.com/sleepview/overview.shtml> (Web pages cached on Feb. 23, 2010, Dec. 29, 2012 and Sep. 4, 2013).
Actigraphy/ Circadian Rhythm SOMNOwatch, URL <http://www.somnomedics.eu/news-events/publications/somnowatchtm.html> (Web page cached on Jan. 23, 2010).
Zio Event Card, URL <http://www.irhythmtech.com/zio-solution/zio-event/> (Web page cached on Mar. 11, 2013).
Zio Patch System, URL <http://www.irhythmtech.com/zio-solution/zio-system/index.html> (Web page cached on Sep. 8, 2013).
Seifert, Dan, "Samsung dives into fitness wearable with the Gear Fit/ the Verge," URL <http://www.theverge.com/2014/2/24/5440310/samsung-dives-into-fitness-wearables-with-the-gear-fit> (Feb. 24, 2014).
Soper, Taylor, "Samsung's new Galaxy S5 flagship phone has fingerprint reader, heart rate monitor," URL <http://www.geekwire.com/2014/samsung-galaxy-s5-fingerprint> (Feb. 24, 2014).
Dolcourt, Jessica, "See the Samsung Galaxy S5's Heart rate monitor in action," URL <http://www.cnet.com/news/see-the-samsung-galaxy-s5s-heart-rate-monitor-in-action> (Feb. 25, 2014).
Saadi et al. "Heart Rhythm Analysis Using ECG Recorded With a Novel Sternum Based Patch Technology—A Pilot Study." Cardio technix 2013—Proceedings of the International Congress on Cardiovascular Technologies, Sep. 20, 2013.
Anonymous. "Omegawave Launches Consumer App 2.0 in U.S. "Endurance Sportswire—Endurance Sportswire. Jul. 11, 2013. URL:http://endurancesportswire.com/omegawave-launches-consumer-app-2-0-in-u-s/.
Chan et al. "Wireless Patch Sensor for Remote Monitoring of Heart Rate, Respiration, Activity, and Falls." pp. 6115-6118. 2013 35th Annual International Conference of the IEEE Engineering in Medical and Biology Society. Jul. 1, 2013.
Daoud et al. "Fall Detection Using Shimmer Technology and Multiresolution Analysis." Aug. 2, 2013. URL: https://decibel.ni.com/content/docs/DOC-26652.
Libbus. "Adherent Cardiac Monitor With Wireless Fall Detection for Patients With Unexplained Syncope." Abstracts of the First AMA-IEEE Medical Technology Conference on Individualized Healthcare. May 22, 2010.
A Voss et al., "Linear and Nonlinear Methods for Analyses of Cardiovascular Variability in Bipolar Disorders," Bipolar Disorders, votl. 8, No. 5p1, Oct. 1, 2006, pp. 441-452, XP55273826, DK ISSN: 1398-5647, DOI: 10.1111/i.1399-5618.2006.00364.x.
"Varicrad-Kardi Software User's Manual Rev. 1.1", Jul. 8, 2009 (Jul. 8, 2009), XP002757888, retrieved from the Internet: URL:http://www.ehrlich.tv/KARDiVAR-Software.pdf [retrieved on May 20, 2016].
"Vedapulse UK," Jan. 1, 2014 (Jan. 1, 2014), XP002757887, Retrieved from the Internet: URL:http://www.vedapulseuk.com/diagnostic/ [retrieved on May 19, 2016].
Duttweiler et al., "Probability Estimation in Arithmetic and Adaptive-Huffman Entropy Coders," IEEE Transactions on Image Processing. vol. 4, No. 3, Mar. 1, 1995, pp. 237-246.
Gupta et al., "An ECG Compression Technique for Telecardiology Application," India Conference (INDICON), 2011 Annual IEEE, Dec. 16, 2011, pp. 1-4.
Nave et al., "ECG Compression Using Long-Term Prediction," IEEE Transactions on Biomedical Engineering, IEEE Service Center, NY, USA, vol. 40, No. 9, Sep. 1, 1993, pp. 877-885.
Skretting et al., "Improved Huffman Coding Using Recursive Splitting," NORSIG, Jan. 1, 1999.
BIOPAC Systems, Inc. #AS148-Automated ECG Analysis , Mar. 24, 2006.
ADINSTRUMENTS:ECG Analysis Module for LabChart & PowerLab, 2008.
https://web.archive.org/web/20130831204020/http://www.biopac.com/research.asp?CatID=37&Main=Software (Aug. 2013).
http://www.gtec.at/Products/Software/g.BSanalyze-Specs-Features (2014).

* cited by examiner

EXTENDED WEAR ELECTROCARDIOGRAPHY PATCH USING INTERLACED WIRE ELECTRODES

CROSS-REFERENCE TO RELATED APPLICATION

This non-provisional patent application is a continuation-in-part of U.S. Pat. No. 9,545,204, issued Jan. 17, 2017, and further claims priority under 35 U.S.C. §119(e) to U.S. Provisional Patent application, Ser. No. 61/882,403, filed Sep. 25, 2013, the disclosures of which are incorporated by reference.

FIELD

This application relates in general to electrocardiographic monitoring and manufacture and, in particular, to an extended wear electrocardiography patch using interlaced wire electrodes.

BACKGROUND

An electrocardiogram (ECG) is a tool used by physicians to diagnose heart problems and other potential health concerns. A full 12-lead ECG provides a multi-vector snapshot of heart function, typically recorded over 12 seconds, that can help diagnose rate and regularity of heartbeats, effect of drugs or cardiac devices, including pacemakers and implantable cardioverter-defibrillators (ICDs), and whether a patient has heart disease of any sort. Full 12-lead ECGs are used in-clinics or hospitals and, as a result, are limited to recording only those heart-related aspects present at the time of recording. Sporadic conditions that may not show up during a 12-second ECG recording require other means to diagnose them. These sporadic conditions include fainting or syncope; rhythm disorders, such as tachyarrhythmias and bradyarrhythmias; apneic episodes; and other cardiac and related disorders. Thus, a 12-lead ECG only provides a partial picture and can be insufficient for complete patient diagnosis of many cardiac disorders.

Diagnostic efficacy of problems, like syncope or cardiac arrhythmias, can be improved through the use of long-term extended wear ECG monitoring. Recording sufficient ECG and related physiological data over an extended period of time remains a significant challenge to healthcare providers, despite over a 40-year history of such efforts. Extended period monitoring essentially enables a physician to identify cardiac conditions, specifically, rhythm disorders, and other physiological events of potential concern. A 30-day observation day period is considered the "gold standard" of ECG monitoring, yet achieving a 30-day observation day period has heretofore proven unworkable because such ECG monitoring systems are arduous to employ, cumbersome to the patient, and excessively costly to manufacture and deploy. Nevertheless, if a patient's ECG could be recorded in an ambulatory setting over prolonged time periods, thereby allowing the patient to engage in activities of daily living, the chances of acquiring meaningful medical information and capturing an abnormal event while the patient is engaged in normal activities becomes more likely to be achieved.

Conventionally, maintaining continual contact between ECG electrodes and the skin after a day or two has been a problem. Time, dirt, moisture, and other environmental contaminants, as well as perspiration, skin oil, and dead skin cells from the patient's body, can get between an ECG electrode's non-conductive adhesive and the skin's surface. All of these factors adversely affect electrode adhesion and the quality of cardiac signal recordings. Furthermore, the physical movements of the patient and their clothing impart various compressional, tensile, and torsional forces on the contact point of an ECG electrode, especially over long recording times, and an inflexibly fastened ECG electrode will be prone to becoming dislodged. Moreover, dislodgment may occur unbeknownst to the patient, making the ECG recordings worthless. Further, some patients may have skin that is susceptible to itching or irritation, and the wearing of ECG electrodes can aggravate such skin conditions. Thus, a patient may want or need to periodically remove or replace ECG electrodes during a long-term ECG monitoring period, whether to replace a dislodged electrode, reestablish better adhesion, alleviate itching or irritation, allow for cleansing of the skin, allow for showering and exercise, or for other purpose. Such replacement or slight alteration in electrode location actually facilitates the goal of recording the ECG signal for long periods of time.

In addition, the high cost of the patient-wearable components used to provide long-term extended ECG monitoring can negatively influence the availability and use of monitors. Ideally, disposable, single-use components, such as adhesive electrodes, should be low cost, while other components of higher complexity, particularly the electronics hardware that detects and records ECG and related physiology, may be of unavoidably higher cost. To a degree, costs can be balanced by designing higher complexity components to be re-usable, but when the total cost of a full ECG monitoring ensemble remains high, despite the utilization of re-usable parts, the number of monitors available for use by healthcare providers can be inhibited. Cost, then, becomes a barrier to entry, which, in turn, can hinder or prevent healthcare providers from obtaining the means with which to efficaciously identify the physiology underlying sporadic cardiac arrhythmic conditions and can ultimately contribute to a failure to make a proper and timely medical diagnosis.

Conventionally, Holter monitors are widely used for long-term extended ECG monitoring. Typically, they are often used for only 24-48 hours. A typical Holter monitor is a wearable and portable version of an ECG that include cables for each electrode placed on the skin and a separate battery-powered ECG recorder. The cable and electrode combination (or leads) are placed in the anterior thoracic region in a manner similar to what is done with an in-clinic standard ECG machine. The duration of a Holter monitoring recording depends on the sensing and storage capabilities of the monitor, as well as battery life. A "looping" Holter (or event) monitor can operate for a longer period of time by overwriting older ECG tracings, thence "recycling" storage in favor of extended operation, yet at the risk of losing event data. Although capable of extended ECG monitoring, Holter monitors are cumbersome, expensive and typically only available by medical prescription, which limits their usability. Further, the skill required to properly place the electrodes on the patient's chest hinders or precludes a patient from replacing or removing the precordial leads and usually involves moving the patient from the physician office to a specialized center within the hospital or clinic.

The ZIO XT Patch and ZIO Event Card devices, manufactured by iRhythm Tech., Inc., San Francisco, Calif., are wearable stick-on monitoring devices that are typically worn on the upper left pectoral region to respectively provide continuous and looping ECG recording. The location is used to simulate surgically implanted monitors. Both of these devices are prescription-only and for single patient use. The ZIO XT Patch device is limited to a 14-day monitoring period, while the electrodes only of the ZIO Event Card device can be worn for up to 30 days. The ZIO XT Patch device combines both electronic recordation components and physical electrodes into a unitary assembly that adheres to the patient's skin. The ZIO XT Patch device uses adhesive sufficiently strong to support the weight of both the monitor and the electrodes over an extended period of time and to resist disadherence from the patient's body, albeit at the cost of disallowing removal or relocation during the monitoring period. The ZIO Event Card device is a form of downsized Holter monitor with a recorder component that must be removed temporarily during baths or other activities that could damage the non-waterproof electronics. Both devices represent compromises between length of wear and quality of ECG monitoring, especially with respect to ease of long term use, female-friendly fit, and quality of cardiac electrical potential signals, especially atrial (P-wave) signals.

Therefore, a need remains for a low cost extended wear continuously recording ECG monitor practicably capable of being worn for a long period of time, especially in patient's whose breast anatomy can interfere with signal quality in both men and women and that is capable of recording atrial action potential signals reliably.

SUMMARY

Physiological monitoring can be provided through a lightweight wearable monitor that includes two components, a flexible extended wear electrode patch and a reusable monitor recorder that removably snaps into a receptacle on the electrode patch. The wearable monitor sits centrally (in the midline) on the patient's chest along the sternum oriented top-to-bottom. The placement of the wearable monitor in a location at the sternal midline (or immediately to either side of the sternum), with its unique narrow "hourglass"-like shape, significantly improves the ability of the wearable monitor to cutaneously sense cardiac electrical potential signals, particularly the P-wave (or atrial activity) and, to a lesser extent, the QRS interval signals indicating ventricular activity in the ECG waveforms.

The electrode patch is shaped to fit comfortably and conformal to the contours of the patient's chest approximately centered on the sternal midline. To counter the dislodgment due to compressional and torsional forces, a layer of non-irritating adhesive, such as hydrocolloid, is provided at least partially on the underside, or contact, surface of the electrode patch, but only on the electrode patch's distal and proximal ends, where the electrode signal pickups are located. The unadhesed narrowed midsection rides freely over the skin. To counter dislodgment due to tensile and torsional forces, a flexible backing is reinforced with a flexible wire interlaced longitudinally through the narrowed midsection, with the curvature of the flexile wire providing both structural support and malleability. Each of these components are distinctive and allow for comfortable and extended wear, especially for women, where breast mobility would otherwise interfere with monitor use and wearer comfort.

Moreover, the interlacing of flexile wire simplifies manufacturing and reduces costs. A simple pair of flexile wires are used, instead of custom point-to-point circuit traces, to connect each electrode signal pickup to the receptacle. One end of each flexile wire can be sewn into the receptacle's circuit board, thereby obviating the need for conductive adhesive, soldered or electromechanical connection, and the other end of each flexile wire, when stripped of insulation, can act as an electrode signal pickup, which lowers component count.

One embodiment provides an extended wear electrocardiography patch using interlaced wire electrodes. A flexible backing is formed of an elongated strip of stretchable material with a narrow longitudinal midsection evenly tapering inward from a distal end and a proximal end, the elongated strip adherable only to a contact surface defined on each of the ends. A pair of flexile wires make up a pair of electrodes, one such electrode comprising one of the flexile wires interlaced into the distal end of the elongated strip and continuing back along an axial path through the narrow longitudinal midsection, another such electrode comprising the other of the flexile wires interlaced into the proximal end of the elongated strip, each of the electrodes further comprising an electrically conductive area only exposed on the contact surface. A circuit board is affixed on the proximal end of the elongated strip, comprising a battery compartment operable to hold a battery for powering an electrocardiography monitor, and an electrical pad operable to electrically couple the electrocardiography monitor with the pair of the electrodes. Alternatively, the circuit board is replaced by a housing that is affixed on the proximal end of the elongated strip, comprising a battery compartment operable to hold a battery for powering an electrocardiography monitor and a plurality of electrical pads operable to electrically couple the electrocardiography monitor with the pair of the electrodes. The housing can be affixed to the proximal end through the interlacing of the flexile wire. A non-conductive receptacle is securely adhered on the one end of the elongated strip opposite the contact surface and formed to removably receive the electrocardiography monitor, the non-conductive receptacle comprising electrode terminals aligned to electrically interface the pair of the flexile wires to the electrocardiography monitor.

A further embodiment provides an extended wear electrocardiography patch using non-metal electrodes. A flexible backing is formed of an elongated strip of stretchable material with a narrow longitudinal midsection evenly tapering inward from a distal end and a proximal end, the elongated strip adherable only to a contact surface defined on each of the ends. A pair of flexile wires makes up a pair of electrodes, one such electrode comprising one of the flexile wires positioned on the distal end of the elongated strip on the contact surface and continuing back along an axial path through the narrow longitudinal midsection, another such electrode comprising the other of the flexile wires positioned on the proximal end of the elongated strip on the contact surface, each of the electrodes being embedded in an electrically conductive non-metal adhesive. A circuit board is affixed on the proximal end of the elongated strip, comprising a battery compartment operable to hold a battery for powering an electrocardiography monitor, and an electrical pad operable to electrically couple the electrocardiography monitor with the pair of the electrodes. Alternatively, the circuit board is replaced by a housing that is affixed on the proximal end of the elongated strip, comprising a battery compartment operable to hold a battery for powering an electrocardiography monitor and a plurality of electrical pads operable to electrically couple the electrocardiography monitor with the pair of the electrodes. The housing can be affixed to the proximal end through the interlacing of the flexile wires. A non-conductive receptacle is securely adhered on the one end of the elongated strip opposite the contact surface and formed to removably receive the electrocardiography monitor, the non-conductive receptacle includes electrode terminals aligned to electrically interface the pair of the flexile wires to the electrocardiography monitor.

The monitoring patch is especially suited to the female anatomy, although also easily used over the male sternum. The narrow longitudinal midsection can fit nicely within the intermammary cleft of the breasts without inducing discomfort, whereas conventional patch electrodes are wide and, if adhered between the breasts, would cause chafing, irritation, discomfort, and annoyance, leading to low patient compliance.

The foregoing aspects enhance ECG monitoring performance and quality by facilitating long-term ECG recording, which is critical to accurate arrhythmia and cardiac rhythm disorder diagnoses.

In addition, the foregoing aspects enhance comfort in women (and certain men), but not irritation of the breasts, by placing the monitoring patch in the best location possible for optimizing the recording of cardiac signals from the atrium, particularly P-waves, which is another feature critical to proper arrhythmia and cardiac rhythm disorder diagnoses.

Further, the interlaced flexile wires improve the dermal electrode's response to tensile, twisting, compressional, and torsional forces by providing a strain relief and tensile strength, while also diminish the cost and complexity of producing physiological electrode assemblies and other types of electrical circuits, where point-to-point interconnections are needed.

Still other embodiments will become readily apparent to those skilled in the art from the following detailed description, wherein are described embodiments by way of illustrating the best mode contemplated. As will be realized, other and different embodiments are possible and the embodiments' several details are capable of modifications in various obvious respects, all without departing from their spirit and the scope. Accordingly, the drawings and detailed description are to be regarded as illustrative in nature and not as restrictive.

DETAILED DESCRIPTION

Figure 1:
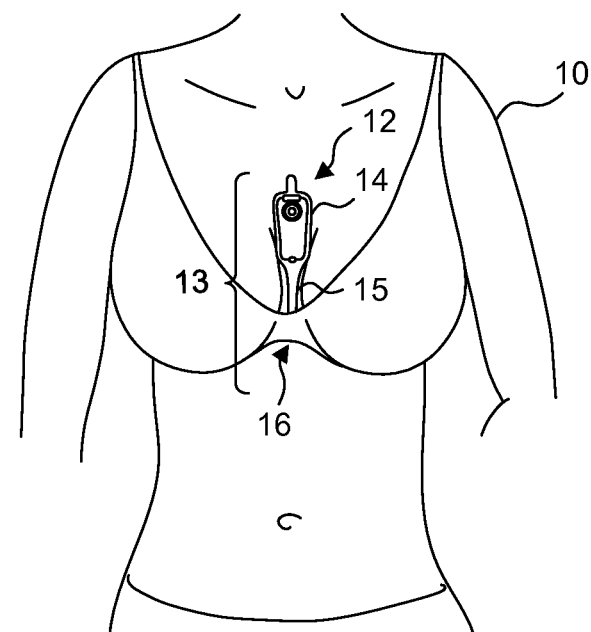
FIGS. 1 and 2 are diagrams showing, by way of examples, an extended wear electrocardiography monitor, including an extended wear electrode patch in accordance with one embodiment, respectively fitted to the sternal region of a female patient and a male patient.
Figure 2:
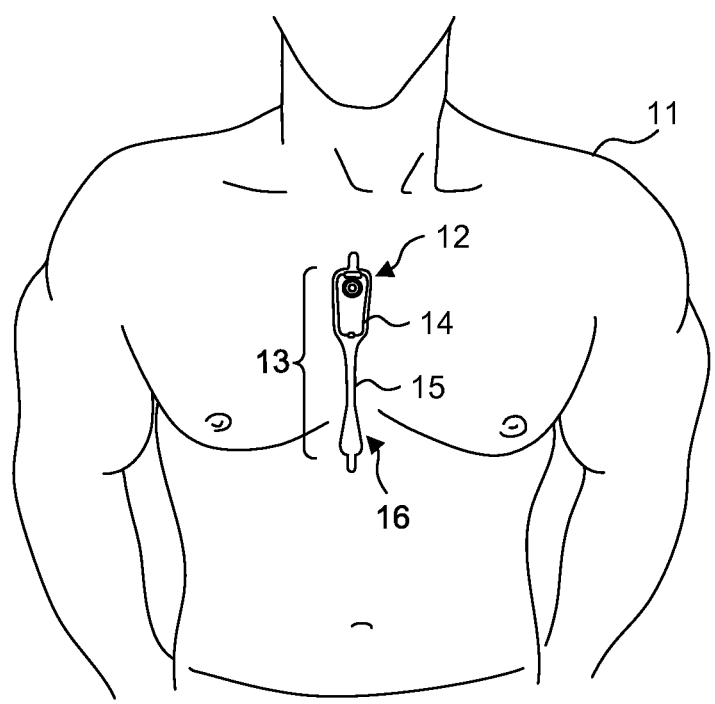

Physiological monitoring can be provided through a wearable monitor that includes two components, a flexible extended wear electrode patch and a removable reusable monitor recorder. FIGS. 1 and 2 are diagrams showing, by way of examples, an extended wear electrocardiography monitor 12, including an extended wear electrode patch 15 in accordance with one embodiment, respectively fitted to the sternal region of a female patient 10 and a male patient 11. The wearable monitor 12 sits centrally (in the midline) on the patient's chest along the sternum 13 oriented top-to-bottom with the monitor recorder 14 preferably situated towards the patient's head. The electrode patch 15 is shaped to fit comfortably and conformal to the contours of the patient's chest approximately centered on the sternal midline 16 (or immediately to either side of the sternum 13). The distal end of the electrode patch 15 extends towards the Xiphoid process and lower sternum and, depending upon the patient's build, may straddle the region over the Xiphoid process and lower sternum. The proximal end of the electrode patch 15, located under the monitor recorder 14, is below the manubrium and, depending upon patient's build, may straddle the region over the manubrium.

The placement of the wearable monitor 12 in a location at the sternal midline 16 (or immediately to either side of the sternum 13) significantly improves the ability of the wearable monitor 12 to cutaneously sense cardiac electric signals, particularly the P-wave (or atrial activity) and, to a lesser extent, the QRS interval signals in the ECG waveforms that indicate ventricular activity. The sternum 13 overlies the right atrium of the heart and the placement of the wearable monitor 12 in the region of the sternal midline 13 puts the ECG electrodes of the electrode patch 15 in a location better adapted to sensing and recording P-wave signals than other placement locations, say, the upper left pectoral region. In addition, placing the lower or inferior pole (ECG electrode) of the electrode patch 15 over (or near) the Xiphoid process and lower sternum facilitates sensing of right ventricular activity and provides superior recordation of the QRS interval.

Figure 3:
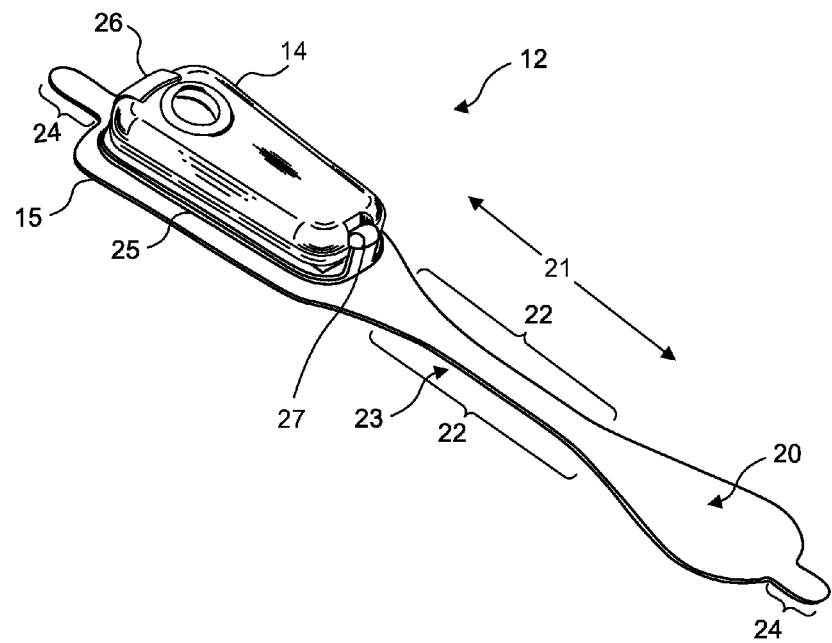
FIG. 3 is a perspective view showing an extended wear electrode patch in accordance with one embodiment with a monitor recorder inserted.

During use, the electrode patch 15 is first adhered to the skin along the sternal midline 16 (or immediately to either side of the sternum 13). A monitor recorder 14 is then snapped into place on the electrode patch 15 to initiate ECG monitoring. FIG. 3 is a perspective view showing an extended wear electrode patch 15 in accordance with one embodiment with a monitor recorder 14 inserted. The body of the electrode patch 15 is preferably constructed using a flexible backing 20 formed as an elongated strip 21 of wrap knit or similar stretchable material about 145 mm long and 32 mm at the widest point with a narrow longitudinal mid-section 23 evenly tapering inward from both sides. A pair of cut-outs 22 between the distal and proximal ends of the electrode patch 15 create a narrow longitudinal midsection 23 or "isthmus" and defines an elongated "hourglass"-like shape, when viewed from above, such as described in commonly-assigned U.S. Design Pat. No. D744,659, issued Dec. 1, 2015, the disclosure of which is incorporated by reference. The upper part of the "hourglass" is sized to allow an electrically non-conductive receptacle 25, sits on top of the outward-facing surface of the electrode patch 15, to be affixed to the electrode patch 15 with an ECG electrode placed underneath on the patient-facing underside, or contact, surface of the electrode patch 15; the upper part of the "hourglass" has a longer and wider profile than the lower part of the "hourglass," which is sized primarily to allow just the placement of an ECG electrode.

The electrode patch 15 incorporates features that significantly improve wearability, performance, and patient comfort throughout an extended monitoring period. The entire electrode patch 15 is lightweight in construction, which allows the patch to be resilient to disadhesing or falling off and, critically, to avoid creating distracting discomfort to the patient, even when the patient is asleep. In contrast, the weight of a heavy ECG monitor impedes patient mobility and will cause the monitor to constantly tug downwards and press on the patient's body; frequent adjustments by the patient are needed to maintain comfort.

During every day wear, the electrode patch 15 is subjected to pushing, pulling, and torsional movements, including compressional and torsional forces when the patient bends forward, and tensile and torsional forces when the patient leans backwards. To counter these stress forces, the electrode patch 15 incorporates crimp and strain reliefs, as further described infra respectively with reference to FIGS. 4 and 5. In addition, the cut-outs 22 and longitudinal midsection 23 help minimize interference with and discomfort to breast tissue, particularly in women (and gynecomastic men). The cut-outs 22 and longitudinal midsection 23 allow better conformity of the electrode patch 15 to sternal bowing and to the narrow isthmus of flat skin that can occur along the bottom of the intermammary cleft between the breasts, especially in buxom women. The cut-outs 22 and longitudinal midsection 23 help the electrode patch 15 fit nicely between a pair of female breasts in the intermammary cleft. In one embodiment, the cut-outs 22 can be graduated to form the longitudinal midsection 23 as a narrow in-between stem or isthmus portion about 7 mm wide. In a still further embodiment, tabs 24 can respectively extend an additional 8 mm to 12 mm beyond the distal and proximal ends of the flexible backing 20 to facilitate purchase when adhering the electrode patch 15 to or removing the electrode patch 15 from the sternum 13. These tabs preferably lack adhesive on the underside, or contact, surface of the electrode patch 15. Still other shapes, cut-outs and conformities to the electrode patch 15 are possible.

The monitor recorder 14 removably and reusably snaps into an electrically non-conductive receptacle 25 during use. The monitor recorder 14 contains electronic circuitry for recording and storing the patient's electrocardiography as sensed via a pair of ECG electrodes provided on the electrode patch 15, such as described in commonly-assigned U.S. Patent Application Publication No. 2015/0087949, the disclosure of which is incorporated by reference. The circuitry includes a microcontroller, flash storage, ECG signal processing, analog-to-digital conversion (where applicable), and an external interface for coupling to the electrode patch 15 and to a download station for stored data download and device programming. The monitor recorder 14 also includes external patient-interfaceable controls, such as a push button to facilitate event marking and provide feedback. In a further embodiment, the circuitry, with the assistance of the appropriate types of deployed electrodes or sensors, is capable of monitoring other types of physiology, in addition to ECGs. Still other types of monitor recorder components and functionality are possible.

The non-conductive receptacle 25 is provided on the top surface of the flexible backing 20 with a retention catch 26 and tension clip 27 molded into the non-conductive receptacle 25 to conformably receive and securely hold the monitor recorder 14 in place. The edges of the bottom surface of the non-conductive receptacle 25 are preferably rounded, and the monitor recorder 14 is nestled inside the interior of the non-conductive receptacle 25 to present a rounded (gentle) surface, rather than a sharp edge at the skin-to-device interface.

The electrode patch 15 is intended to be disposable. The monitor recorder 14, however, is reusable and can be transferred to successive electrode patches 15 to ensure continuity of monitoring. The placement of the wearable monitor 12 in a location at the sternal midline 16 (or immediately to either side of the sternum 13) benefits long-term extended wear by removing the requirement that ECG electrodes be continually placed in the same spots on the skin throughout the monitoring period. Instead, the patient is free to place an electrode patch 15 anywhere within the general region of the sternum 13.

As a result, at any point during ECG monitoring, the patient's skin is able to recover from the wearing of an electrode patch 15, which increases patient comfort and satisfaction, while the monitor recorder 14 ensures ECG monitoring continuity with minimal effort. A monitor recorder 14 is merely unsnapped from a worn out electrode patch 15, the worn out electrode patch 15 is removed from the skin, a new electrode patch 15 is adhered to the skin, possibly in a new spot immediately adjacent to the earlier location, and the same monitor recorder 14 is snapped into the new electrode patch 15 to reinitiate and continue the ECG monitoring.

Figure 4:
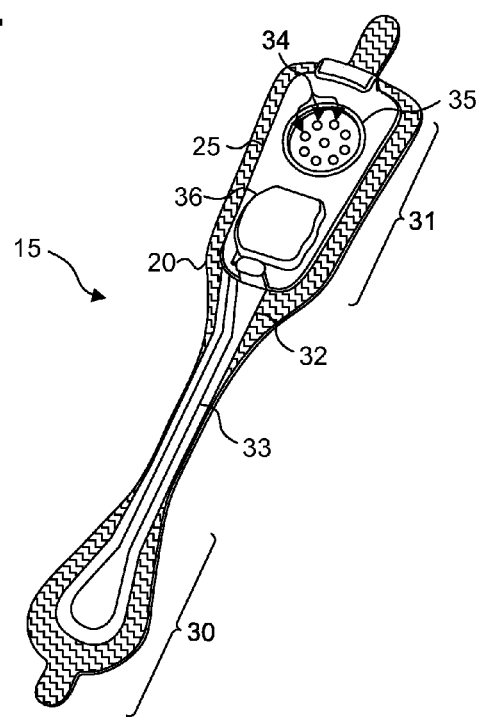
FIG. 4 is a perspective view showing the extended wear electrode patch of FIG. 3 without a monitor recorder inserted.

During use, the electrode patch 15 is first adhered to the skin in the sternal region. FIG. 4 is a perspective view showing the extended wear electrode patch 15 of FIG. 3 without a monitor recorder 14 inserted. A flexible circuit 32 is adhered to each end of the flexible backing 20. A distal circuit trace 33 from the distal end 30 of the flexible backing 20 and a proximal circuit trace (not shown) from the proximal end 31 of the flexible backing 20 electrically couple ECG electrodes (not shown) with a pair of electrical pads 34. In a further embodiment, the distal and proximal circuit traces are replaced with interlaced or sewn-in flexible wires, as further described infra beginning with reference to FIG. 9. The electrical pads 34 are provided within a moisture-resistant seal 35 formed on the bottom surface of the non-conductive receptacle 25. When the monitor recorder 14 is securely received into the non-conductive receptacle 25, that is, snapped into place, the electrical pads 34 interface to electrical contacts (not shown) protruding from the bottom surface of the monitor recorder 14. The moisture-resistant seal 35 enables the monitor recorder 14 to be worn at all times, even during bathing or other activities that could expose the monitor recorder 14 to moisture or adverse conditions.

In addition, a battery compartment 36 is formed on the bottom surface of the non-conductive receptacle 25. A pair of battery leads (not shown) from the battery compartment 36 to another pair of the electrical pads 34 electrically interface the battery to the monitor recorder 14. The battery contained within the battery compartment 35 can be replaceable, rechargeable or disposable.

The monitor recorder 14 draws power externally from the battery provided in the non-conductive receptacle 25, thereby uniquely obviating the need for the monitor recorder 14 to carry a dedicated power source. The battery contained within the battery compartment 36 can be replaceable, rechargeable or disposable. In a further embodiment, the ECG sensing circuitry of the monitor recorder 14 can be supplemented with additional sensors, including an $SpO_2$ sensor, a blood pressure sensor, a temperature sensor, respiratory rate sensor, a glucose sensor, an air flow sensor, and a volumetric pressure sensor, which can be incorporated directly into the monitor recorder 14 or onto the non-conductive receptacle 25.

The placement of the flexible backing 20 on the sternal midline 16 (or immediately to either side of the sternum 13) also helps to minimize the side-to-side movement of the wearable monitor 12 in the left- and right-handed directions during wear. However, the wearable monitor 12 is still susceptible to pushing, pulling, and torquing movements, including compressional and torsional forces when the patient bends forward, and tensile and torsional forces when the patient leans backwards. To counter the dislodgment of the flexible backing 20 due to compressional and torsional forces, a layer of non-irritating adhesive, such as hydrocolloid, is provided at least partially on the underside, or contact, surface of the flexible backing 20, but only on the distal end 30 and the proximal end 31. As a result, the underside, or contact surface of the longitudinal midsection 23 does not have an adhesive layer and remains free to move relative to the skin. Thus, the longitudinal midsection 23 forms a crimp relief that respectively facilitates compression and twisting of the flexible backing 20 in response to compressional and torsional forces. Other forms of flexible backing crimp reliefs are possible.

Figure 5:
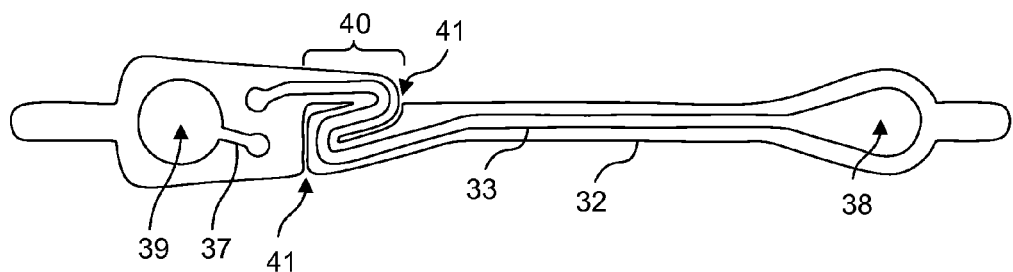
FIG. 5 is a top view showing the flexible circuit of the extended wear electrode patch of FIG. 3.

Unlike the flexible backing 20, the flexible circuit 32 is only able to bend and cannot stretch in a planar direction. FIG. 5 is a top view showing the flexible circuit 32 of the extended wear electrode patch 15 of FIG. 3. A distal ECG electrode 38 and proximal ECG electrode 39 are respectively coupled to the distal and proximal ends of the flexible circuit 32 to serve as electrode signal pickups. The flexible circuit 32 preferably does not extend to the outside edges of the flexible backing 20, thereby avoiding gouging or discomforting the patient's skin during extended wear, such as when sleeping on the side. During wear, the ECG electrodes 38, 39 must remain in continual contact with the skin. A strain relief 40 is defined in the flexible circuit 32 at a location that is partially underneath the battery compartment 36 when the flexible circuit 32 is affixed to the flexible backing 20. The strain relief 40 is laterally extendable to counter dislodgment of the ECG electrodes 38, 39 due to tensile and torsional forces. A pair of strain relief cutouts 41 partially extend transversely from each opposite side of the flexible circuit 32 and continue longitudinally towards each other to define in 'S'-shaped pattern, when viewed from above. The strain relief respectively facilitates longitudinal extension and twisting of the flexible circuit 32 in response to tensile and torsional forces. Other forms of circuit board strain relief are possible.

Figure 6:
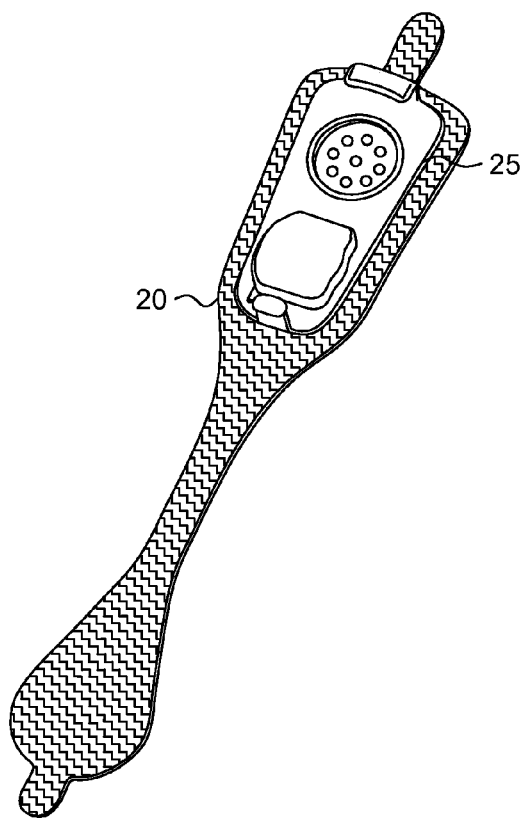
FIG. 6 is a perspective view showing the extended wear electrode patch in accordance with a further embodiment.

The flexible circuit 32 can be provided either above or below the flexible backing 20. FIG. 6 is a perspective view showing the extended wear electrode patch 15 in accordance with a further embodiment. The flexible circuit (not shown) is provided on the underside, or contact, surface of the flexible backing 20 and is electrically interfaced to the set of electrical pads 34 on the bottom surface of the non-conductive receptacle 25 through electrical contacts (not shown) pierced through the flexible backing 20.

Figure 7:
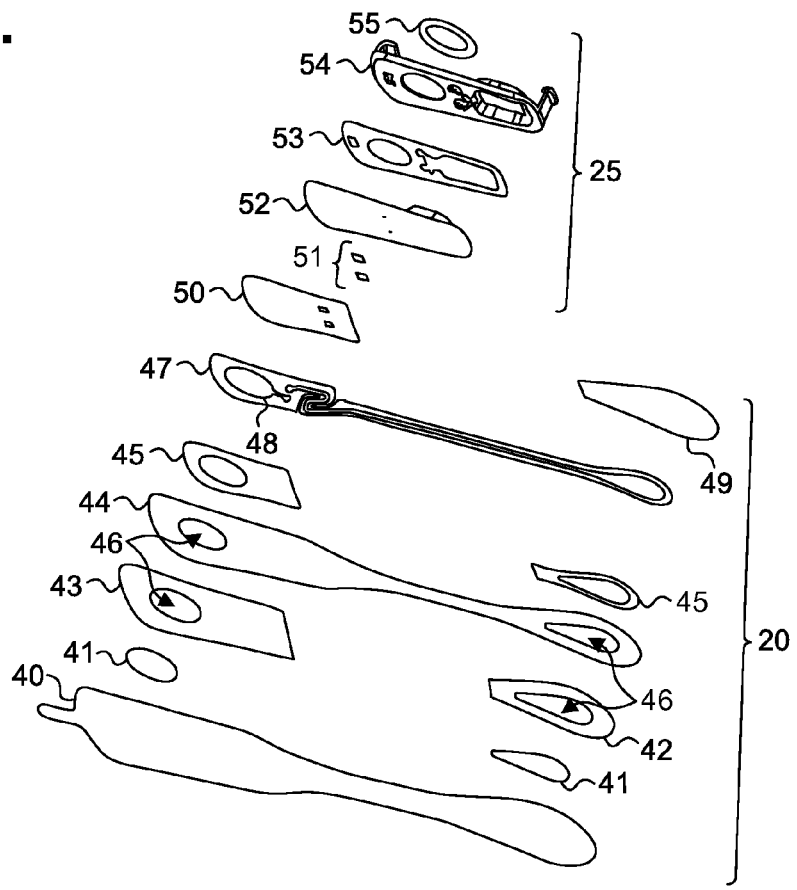
FIG. 7 is an exploded view showing the component layers of the electrode patch of FIG. 3.

The electrode patch 15 is intended to be a disposable component, which enables a patient to replace the electrode patch 15 as needed throughout the monitoring period, while maintaining continuity of physiological sensing through reuse of the same monitor recorder 14. FIG. 7 is an exploded view showing the component layers of the electrode patch 15 of FIG. 3. The flexible backing 20 is constructed of a wearable gauze, latex, woven textile, or similar wrap knit or stretchable and wear-safe material 44, such as a Tricot-type linen with a pressure sensitive adhesive (PSA) on the underside, or contact, surface. The ends of the wearable material 44 are coated with a layer 43 of non-irritating adhesive, such as hydrocolloid, to facilitate long-term wear, while the unadhesed narrowed midsection rides freely over the skin. The hydrocolloid, for instance, is typically made of mineral oil, cellulose and water and lacks any chemical solvents, so should cause little itching or irritation. Moreover, hydrocolloid can be manufactured into an appropriate thickness and plasticity and provides cushioning between the relatively rigid and unyielding non-conductive receptacle 25 and the patient's skin. In a further embodiment, the layer of non-irritating adhesive can be contoured, such as by forming the adhesive with a concave or convex cross-section; surfaced, such as through stripes or crosshatches of adhesive, or by forming dimples in the adhesive's surface; or applied discontinuously, such as with a formation of discrete dots of adhesive.

As described supra with reference to FIG. 5, a flexible circuit can be adhered to either the outward facing surface or the underside, or contact, surface of the flexible backing 20. For convenience, a flexible circuit 47 is shown relative to the outward facing surface of the wearable material 44 and is adhered respectively on a distal end by a distal electrode seal 45 and on a proximal end by a proximal electrode seal 45. In a further embodiment, the flexible circuit 47 can be provided on the underside, or contact, surface of the wearable material 44. Through the electrode seals, only the distal and proximal ends of the flexible circuit 47 are attached to the wearable material 44, which enables the strain relief 40 (shown in FIG. 5) to respectively longitudinally extend and twist in response to tensile and torsional forces during wear. Similarly, the layer 43 of non-irritating adhesive is provided on the underside, or contact, surface of the wearable material 44 only on the proximal and distal ends, which enables the longitudinal midsection 23 (shown in FIG. 3) to respectively bow outward and away from the sternum 13 or twist in response to compressional and torsional forces during wear.

Figure 8:
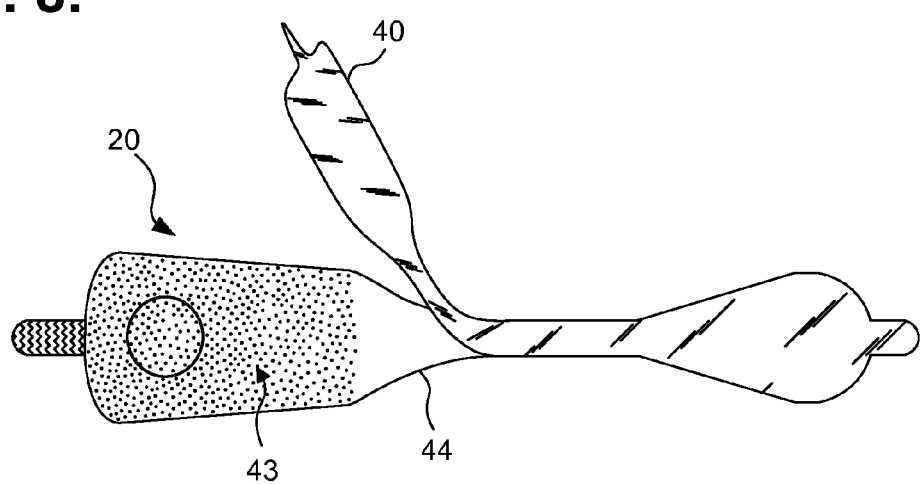
FIG. 8 is a bottom plan view of the extended wear electrode patch of FIG. 3 with liner partially peeled back.

A pair of openings 46 is defined on the distal and proximal ends of the wearable material 44 and layer 43 of non-irritating adhesive for ECG electrodes 38, 39 (shown in FIG. 5). The openings 46 serve as "gel" wells with a layer of hydrogel 41 being used to fill the bottom of each opening 46 as a conductive material that aids electrode signal capture. The entire underside, or contact, surface of the flexible backing 20 is protected prior to use by a liner layer 40 that is peeled away, as shown in FIG. 8.

The non-conductive receptacle 25 includes a main body 54 that is molded out of polycarbonate, ABS, or an alloy of those two materials to provide a high surface energy to facilitate adhesion of an adhesive seal 53. The main body 54 is attached to a battery printed circuit board 52 by the adhesive seal 53 and, in turn, the battery printed circuit board 52 is adhered to the flexible circuit 47 with an upper flexible circuit seal 50. A pair of conductive transfer adhesive points 51 or, alternatively, soldered connections, or electromechanical connections, including metallic rivets or similar conductive and structurally unifying components, connect the circuit traces 33, 37 (shown in FIG. 5) of the flexible circuit 47 to the battery printed circuit board 52. The main body 54 has a retention catch 26 and tension clip 27 (shown in FIG. 3) that fixably and securely receive a monitor recorder 14 (not shown), and includes a recess within which to circumferentially receive a die cut gasket 55, either rubber, urethane foam, or similar suitable material, to provide a moisture resistant seal to the set of pads 34. Other types of design, arrangement, and permutation are possible.

Figure 9:
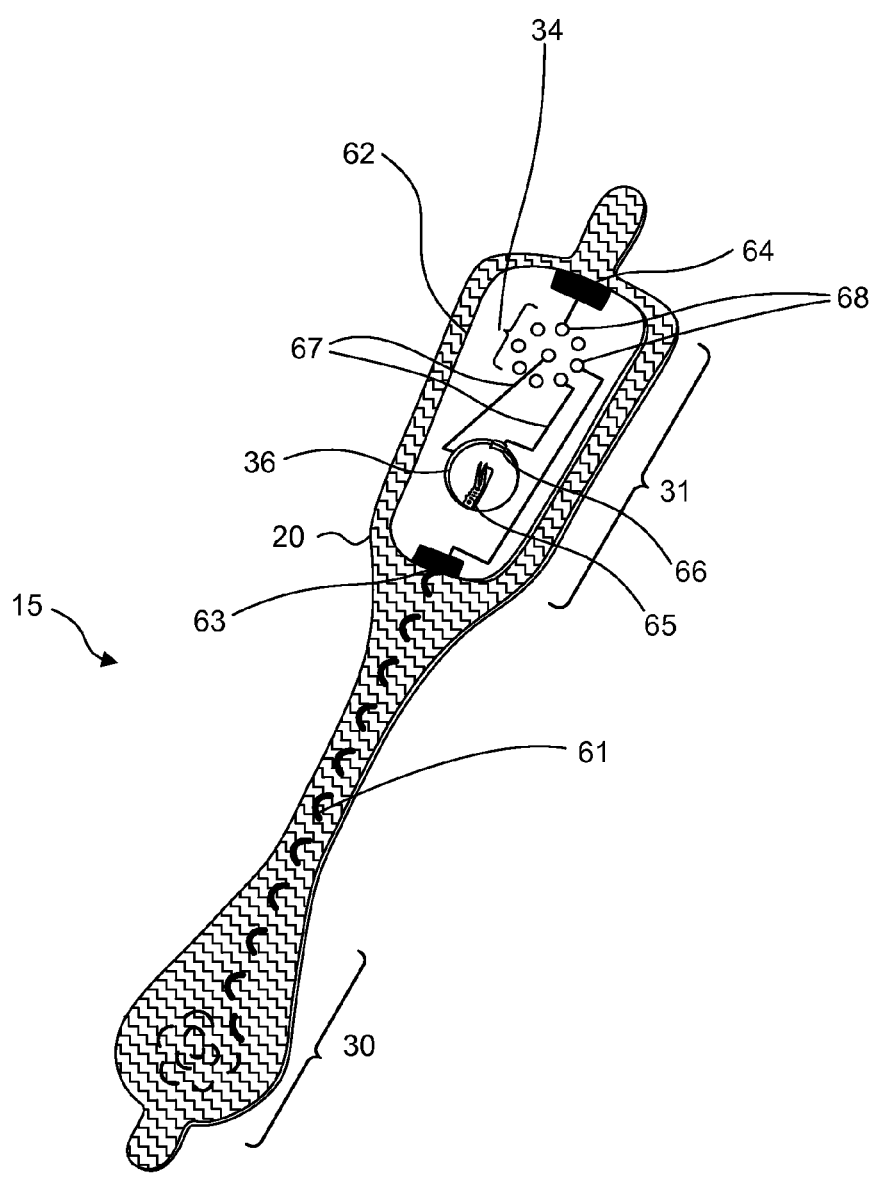
FIG. 9 is a perspective view of an extended wear electrode patch with a flexile wire electrode assembly in accordance with a still further embodiment.

In a still further embodiment, the flexible circuit 32 (shown in FIG. 4) and distal ECG electrode 38 and proximal ECG electrode 39 (shown in FIG. 5) are replaced with a pair of interlaced flexile wires. The interlacing of flexile wires through the flexible backing 20 reduces both manufacturing costs and environmental impact, as further described infra. The flexible circuit and ECG electrodes are replaced with a pair of flexile wires that serve as both electrode circuit traces and electrode signal pickups. FIG. 9 is a perspective view of an extended wear electrode patch 15 with a flexile wire electrode assembly in accordance with a still further embodiment. The flexible backing 20 maintains the unique narrow "hourglass"-like shape that aids long term extended wear, particularly in women, as described supra with reference to FIG. 3. For clarity, the non-conductive receptacle 25 is omitted to show the exposed battery printed circuit board 62 that is adhered underneath the non-conductive receptacle 25 to the proximal end 31 of the flexible backing 20. Instead of employing flexible circuits, a pair of flexile wires are separately interlaced or sewn into the flexible backing 20 to serve as circuit connections for an anode electrode lead and for a cathode electrode lead.

To form a distal electrode assembly, a distal wire 61 is interlaced into the distal end 30 of the flexible backing 20, continues along an axial path through the narrow longitudinal midsection of the elongated strip, and electrically connects to the battery printed circuit board 62 on the proximal end 31 of the flexible backing 20. The distal wire 61 is connected to the battery printed circuit board 62 by stripping the distal wire 61 of insulation, if applicable, and interlacing or sewing the uninsulated end of the distal wire 61 directly into an exposed circuit trace 63. The distal wire-to-battery printed circuit board connection can be made, for instance, by back stitching the distal wire 61 back and forth across the edge of the battery printed circuit board 62. Similarly, to form a proximal electrode assembly, a proximal wire (not shown) is interlaced into the proximal end 31 of the flexible backing 20. The proximal wire is connected to the battery printed circuit board 62 by stripping the proximal wire of insulation, if applicable, and interlacing or sewing the uninsulated end of the proximal wire directly into an exposed circuit trace 64. The resulting flexile wire connections both establish electrical connections and help to affix the battery printed circuit board 62 to the flexible backing 20.

The battery printed circuit board 62 is provided with a battery compartment 36. A set of electrical pads 34 are formed on the battery printed circuit board 62. The electrical pads 34 electrically interface the battery printed circuit board 62 with a monitor recorder 14 when fitted into the non-conductive receptacle 25. The battery compartment 36 contains a spring 65 and a clasp 66, or similar assembly, to hold a battery (not shown) in place and electrically interfaces the battery to the electrical pads 34 through a pair battery leads 67 for powering the electrocardiography monitor 14. Other types of battery compartment are possible. The battery contained within the battery compartment 36 can be replaceable, rechargeable, or disposable.

In a yet further embodiment, the circuit board and non-conductive receptacle 25 are replaced by a combined housing that includes a battery compartment and a plurality of electrical pads. The housing can be affixed to the proximal end of the elongated strip through the interlacing or sewing of the flexile wires or other wires or threads.

The core of the flexile wires may be made from a solid, stranded, or braided conductive metal or metal compounds. In general, a solid wire will be less flexible than a stranded wire with the same total cross-sectional area, but will provide more mechanical rigidity than the stranded wire. The conductive core may be copper, aluminum, silver, or other material. The pair of the flexile wires may be provided as insulated wire. In one embodiment, the flexile wires are made from a magnet wire from Belden Cable, catalogue number 8051, with a solid core of AWG 22 with bare copper as conductor material and insulated by polyurethane or nylon. Still other types of flexile wires are possible. In a further embodiment, conductive ink or graphene can be used to print electrical connections, either in combination with or in place of the flexile wires.

Figure 10:
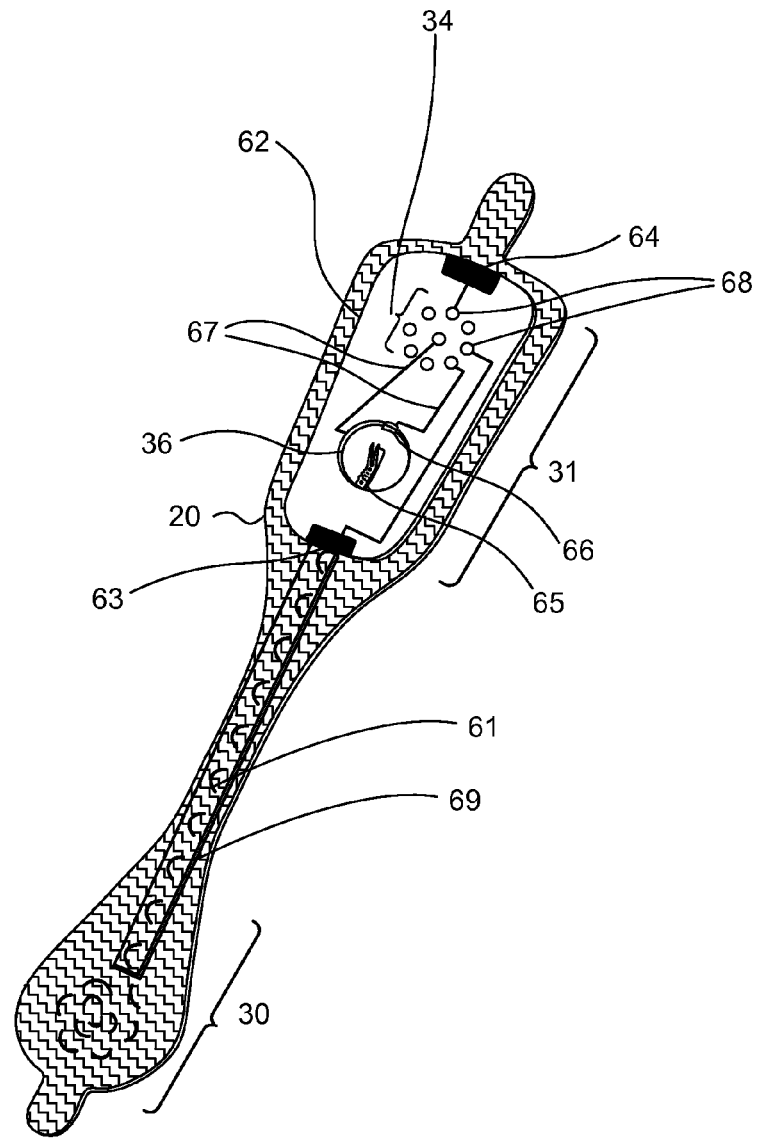
FIG. 10 is perspective view of the flexile wire electrode assembly from FIG. 9, with a layer of insulating material shielding a bare distal wire around the midsection of the flexible backing

In a still further embodiment, the flexile wires are uninsulated. FIG. 10 is perspective view of the flexile wire electrode assembly from FIG. 9, with a layer of insulating material 69 shielding a bare uninsulated distal wire 61 around the midsection on the contact side of the flexible backing. On the contact side of the proximal and distal ends of the flexible backing, only the portions of the flexile wires serving as electrode signal pickups are electrically exposed and the rest of the flexile wire on the contact side outside of the proximal and distal ends are shielded from electrical contact. The bare uninsulated distal wire 61 may be insulated using a layer of plastic, rubber-like polymers, or varnish, or by an additional layer of gauze or adhesive (or non-adhesive) gel. The bare uninsulated wire 61 on the non-contact side of the flexible backing may be insulated or can simply be left uninsulated.

Figure 11:
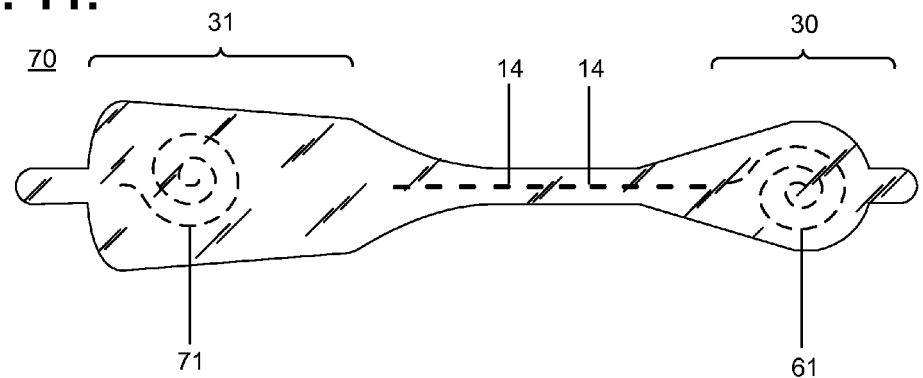
FIG. 11 is a bottom view of the flexile wire electrode assembly as shown in FIG. 9.

Both end portions of the pair of flexile wires are typically placed uninsulated on the contact surface of the flexible backing 20 to form a pair of electrode signal pickups. FIG. 11 is a bottom view of the flexile wire electrode assembly as shown in FIG. 9. When adhered to the skin during use, the uninsulated end portions of the distal wire 61 and the proximal wire 71 enable the monitor recorder 14 to measure dermal electrical potential differentials. At the proximal and distal ends of the flexible backing 20, the uninsulated end portions of the flexile wires may be configured into an appropriate pattern to provide an electrode signal pickup, which would typically be a spiral shape formed by guiding the flexile wire along an inwardly spiraling pattern. The surface area of the electrode pickups can also be variable, such as by selectively removing some or all of the insulation on the contact surface. For example, an electrode signal pickup arranged by sewing insulated flexile wire in a spiral pattern could have a crescent-shaped cutout of uninsulated flexile wire facing towards the signal source.

Figure 12:
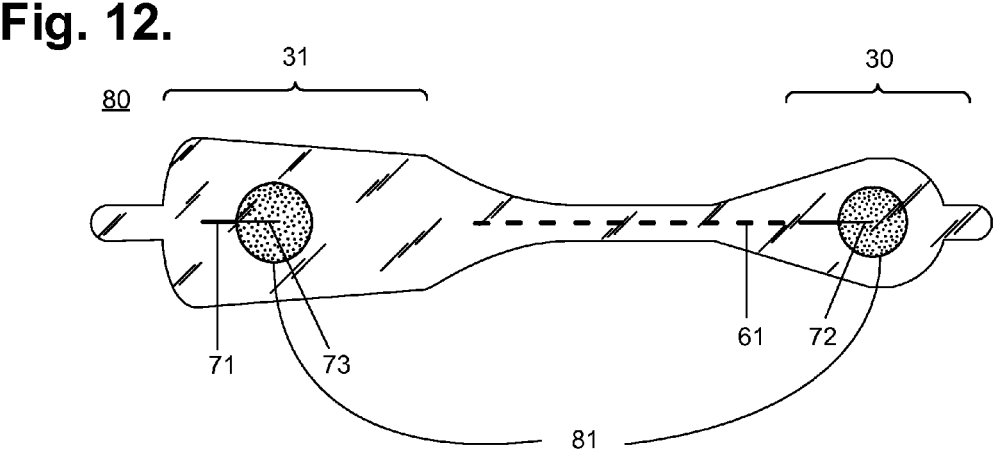
FIG. 12 is a bottom view of a flexile wire electrode assembly in accordance with a still yet further embodiment.

In a still yet further embodiment, the flexile wires are left freely riding on the contact surfaces on the distal and proximal ends of the flexible backing, rather than being interlaced into the ends of the flexible backing 20. FIG. 12 is a bottom view of a flexile wire electrode assembly in accordance with a still yet further embodiment. The distal wire 61 is interlaced onto the midsection and extends an exposed end portion 72 onto the distal end 30. The proximal wire 71 extends an exposed end portion 73 onto the proximal end 31. The exposed end portions 72 and 73, not shielded with insulation, are further embedded within an electrically conductive adhesive 81. The adhesive 81 makes contact to skin during use and conducts skin electrical potentials to the monitor recorder 14 (not shown) via the flexile wires. The adhesive 81 can be formed from electrically conductive, non-irritating adhesive, such as hydrocolloid.

Figure 13:
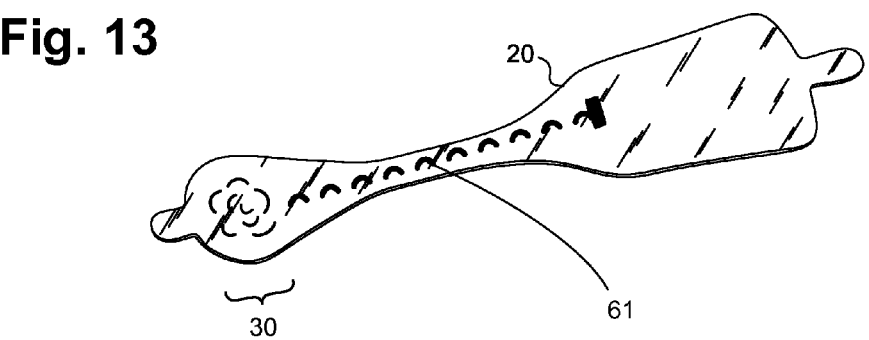
FIG. 13 is a perspective view showing the longitudinal midsection of the flexible backing of the electrode assembly from FIG. 9.

The distal wire 61 is interlaced or sewn through the longitudinal midsection of the flexible backing 20 and takes the place of the flexible circuit 32. FIG. 13 is a perspective view showing the longitudinal midsection of the flexible backing of the electrode assembly from FIG. 9. Various stitching patterns may be adopted to provide a proper combination of rigidity and flexibility. In simplest form, the distal wire 61 can be manually threaded through a plurality of holes provided at regularly-spaced intervals along an axial path defined between the battery printed circuit board 62 (not shown) and the distal end 30 of the flexible backing 20. The distal wire 61 can be threaded through the plurality of holes by stitching the flexile wire as a single "thread." Other types of stitching patterns or stitching of multiple "threads" could also be used, as well as using a sewing machine or similar device to machine-stitch the distal wire 61 into place, as further described infra. Further, the path of the distal wire 61 need not be limited to a straight line from the distal to the proximal end of the flexible backing 20.

Figure 14:
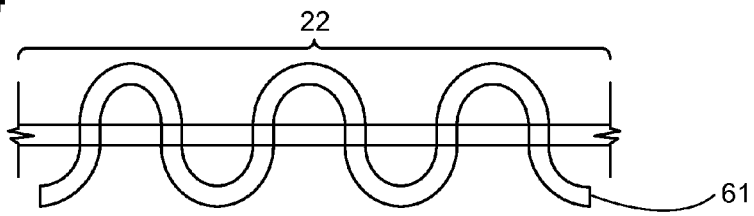
FIG. 14 is a longitudinal cross-sectional view of the midsection of the flexible backing of the electrode assembly of FIG. 11.
Figure 15A:
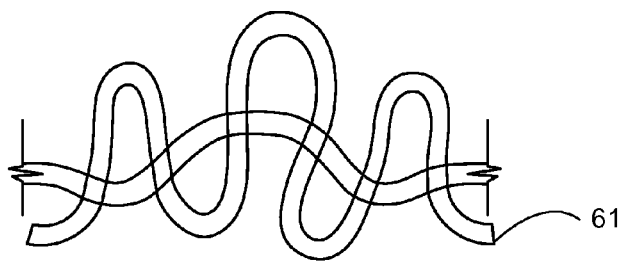
FIGS. 15A-C are the electrode assembly from FIG. 14 under compressional, tensile, and bending force, respectively.
Figure 15B:
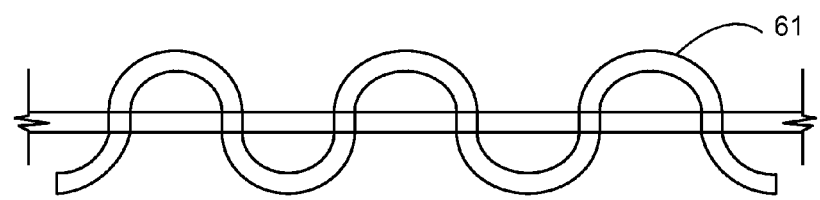
Figure 15C:
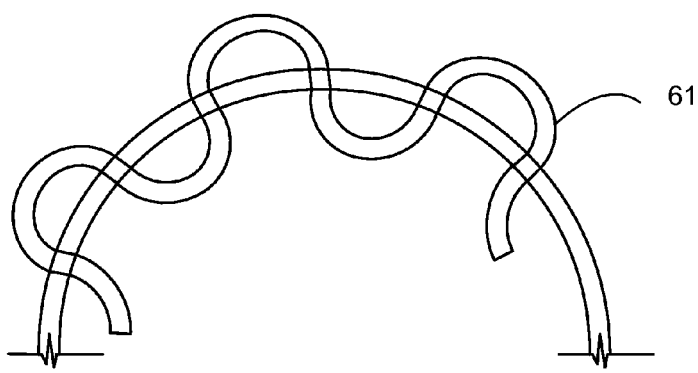

The distal wire 61 is flexile yet still retains a degree of rigidity that is influenced by wire gauge, composition, stranding, insulation, and stitching pattern. For example, rigidity decreases with wire gauge; and a solid core wire tends to be more rigid than a stranded core of the same gauge. The combination of the flexibility and the rigidity of the portion of the distal wire 61 located on or close to the midsection contributes to the overall strength and wearability of the patch. FIG. 14 is a longitudinal cross-sectional view of the midsection of the flexible backing 20 of the electrode assembly of FIG. 11. FIGS. 15A-C are the electrode assembly from FIG. 14 under compressional, tensile, and bending force, respectively. The relative sizes of the distal wire 61 and flexible backing 20 are not to scale and are exaggerated for purposes of illustration.

The interlacing of the distal wire 61 through the narrow longitudinal midsection 22 of the flexible backing 20 bends the distal wire 61 into a line of rounded stitches that alternate top and bottom, which can be advantageous to long term wearability. First, the tension of the rounded stitches reinforces the planar structure of the narrow longitudinal midsection 22 and spreads a dislodging force impacting on one end of the flexible backing 20 to the other end of the flexible backing 20. Second, the rounded stitches leave room for stretching, compressing, bending, and twisting, thus increasing the wearability of the patch extended wear electrode patch 15 by facilitating extension, compression, bending, and twisting of the narrow longitudinal midsection 22 in response to tensile, compressional, bending, and torsional forces.

In a further embodiment, the distal wire and the proximal wire may be stitched or sewn into the flexible backing 20. Depending upon the type of stitching used, the distal or proximal wire may use more than one individual wire. For instance, a conventional sewing machine used to stitch fabrics uses a spool of thread and a bobbin, which are both wound with thread that together allow the creation of various stitching patterns, such as the lockstitch. Other type of stitching patterns are possible. Additionally, where more than one "threads" are used for stitching, the flexile wire may constitute all of the "threads," thereby increasing redundancy of the circuit trace thus formed. Alternatively, just one (or fewer than all) of the threads may be conductive, with the non-conductive threads serving to reinforce the strength of the flexile wire connections and flexible backing 20. The additional threads can be made from line, threads, or fabrics of sufficient mechanical strength and do not need to be conductive; alternatively, the same flexile wires can be employed to serve as the additional threads.

Conventionally, flexible circuits, such as the flexible circuit 32 (shown in FIG. 4) that connects the distal ECG electrode 38 and proximal ECG electrode 39 (shown in FIG. 5) to the battery printed circuit board 62 (shown in FIG. 9), are constructed using subtractive processes. In general, a flexible circuit interconnects electronic components with custom point-to-point circuit traces and is typically constructed by forming the conductive circuit traces on a thin film of insulating polymer. A flexible circuit is not an off-the-shelf component; rather, each flexible circuit is designed with a specific purpose in mind. Changes to a flexible circuit's design will generally require fabricating entirely new flexible circuits, as the physical circuit traces on the polymer film cannot be changed.

Manufacturing a flexible circuit typically requires the use of sophisticated and specialized tools, coupled with environmentally unfriendly processes, including depositing copper on a polyamide core, etching away unwanted copper with inline etching or an acid bath to retain only the desired conductive circuit traces, and applying a coverlay to the resulting flexible circuit. Significant amounts of hazardous waste are generated by these subtractive processes during the fabrication of each flexible circuit. Properly disposing of such hazardous waste is expensive and adds to the costs of the flexible circuit.

In the still further embodiment described supra beginning with reference to FIG. 9, the distal and proximal flexile wires replace the flexible circuit 32 and enables the electrode assembly to be constructed using additive processes with off-the-shelf, low cost components. The flexile wires serve the triple functions of an electrode signal pickup, electrical circuit trace, and support for structural integrity and malleability of the electrode assembly.

The general manner of constructing the electrode assembly can be applied to other forms of electronic components in which custom point-to-point circuit traces need to be affixed to a gauze or textile backing, as well as backings made from other materials. The circuit traces are replaced by the interlaced or sewn flexile wires, and the ends of each flexile wire are terminated, as appropriate to the application. The flexile wires may, by example, connect two circuit boards, or connect to an electrical terminal, power source, or electrical component. In addition, flexile wires may be used to replace a printed circuit board entirely, with each flexile wire serving as a form of sewn interconnect between two or more discrete components, including resistors, capacitors, transistors, diodes, operational amplifiers (op amps) and other integrated circuits, and other electronic or electromechanical components.

Figure 16:
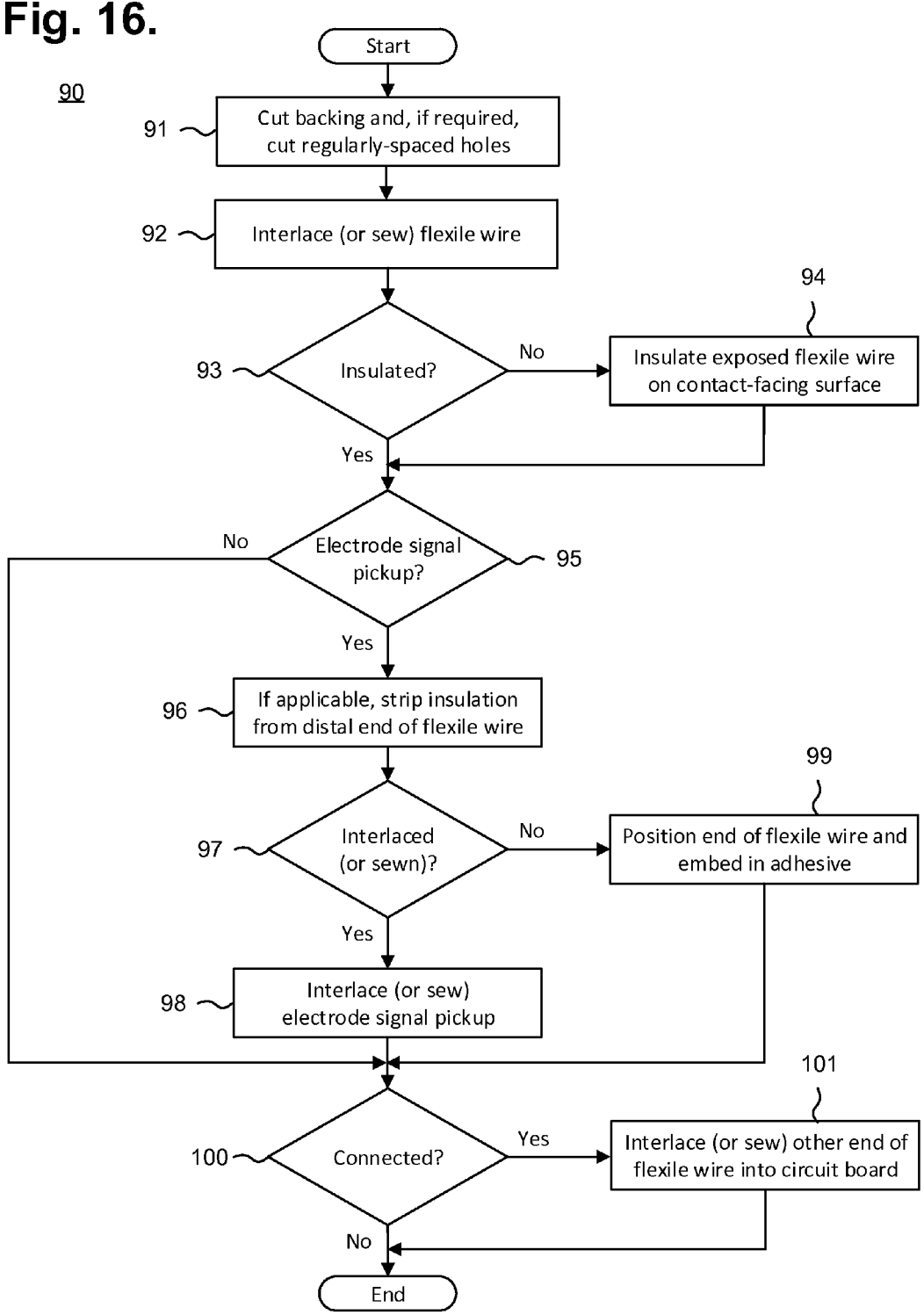
FIG. 16 is a flow diagram showing a method for constructing a stress-pliant physiological electrode assembly in accordance with a further embodiment.

By way of illustration, the flexile wires will be described as terminated for use in an electrode assembly, specifically, as terminated on one end to form an electrode signal pickup and on the other end to connect into a circuit board. Constructing the electrode assembly entails interlacing, including manually threading, or machine sewing the flexile, conductive wire through the flexible backing 20. FIG. 16 is a flow diagram showing a method 90 for constructing a stress-pliant physiological electrode assembly in accordance with a further embodiment. The method can be performed by a set of industrial machines, including a gauze cutting machine to cut the flexible backing 20 to form; a hole punch to cut a plurality of holes provided at regularly-spaced intervals; a stitching or sewing machine to interleave or sew the flexile wire through the flexible backing 20; a wire stripper or plasma jet to remove insulation from the flexile wire, when applicable; and a glue or adhesive dispenser to embed or coat electrode signal pickup in hydrocolloid gel or equivalent non-irritating adhesive. Other forms or combinations of industrial machines, including a single purpose-built industrial machine, could be used.

As an initial step, a backing is cut to shape and, if required, holes are cut at regularly-spaced intervals along an axial path (step 91) through which the flexile wire will be interlaced. Holes will need to be cut, for instance, if the flexile wire is to be hand-guided through the backing, or where the backing is cut from a material that is difficult to puncture with a threaded needle, such as used by a sewing machine. In one embodiment, the backing is cut from wearable gauze, latex, woven textile, or similar wrap knit or stretchable and wear-safe material, such as a Tricot-type linen; the resulting backing is flexible and yielding. The backing is also cut into an elongated "hourglass"-like shape, when viewed from above, with a pair of cut-outs and a longitudinal midsection that together help minimize interference with and discomfort to breast tissue, particularly in women (and gynecomastic men), such as described supra with reference to FIG. 3. The backing can be cut into other shapes as appropriate to need. In addition, depending upon the application, other materials could be substituted for the backing. For example, neoprene, such as used in wetsuits, could be used where a high degree of elasticity and ruggedness is desired.

The flexile wire is then interlaced or sewn into the backing (step 92). Interlacing can be performed by a machine that guides the flexile wire through the holes previously cut in the material in a crisscrossed, interwoven, or knitted fashion, as well as by hand. The flexile wire can also be guided through the backing without first cutting holes, provided that the weave of the material is sufficiently loose to allow passage of the flexile wire if the flexile wire is otherwise incapable of passing through the backing without the assistance of a needle or other piercing instrument.

Alternatively, the flexile wire could be sewn into the backing by using the flexile wire as "thread" that is stitched into place using a needle or similar implement. If a single flexile wire is employed, the stitching will be a line of rounded stitches that alternate top and bottom, as described supra; however, if more than one flexile wire is used, or the stitching pattern requires the use of more than one thread, other forms of conventional machine-stitching patterns could be employed, such as a lockstitch.

Once completed, the interlacing or sewing of the flexile wire into the backing creates an integrated point-to-point electrical path that takes the place of a custom circuit trace using an additive, rather than subtractive, manufacturing process. The flexile wire can be interlaced or sewn along a straight, curved, or arbitrary path. One flexile wire is required per point-to-point circuit trace. The strength and pliability of the flexile wire reinforces the backing and, in the still further embodiment described supra beginning with reference to FIG. 9, facilitates extension, compression, bending, and twisting of the narrow longitudinal midsection 22 in response to tensile, compressional, bending, and torsional forces. Thus, the path of the flexile wire along the backing can be mapped to take advantage of the strength and reinforcing properties of the flexile wire, which, when interlaced or sewn into the backing, help the backing counter the stresses to which the backing will be subjected when deployed.

The flexile wire itself may be insulated or bare (step 93). When one end of the flexile wire is connected to (or forms) an electrode, particularly a dermal physiology electrode that senses electrical potentials on the skin's surface, insulated flexile wire will ordinarily be used, with only a portion of the flexile wire incident to the electrode stripped of insulation. However, bare uninsulated flexile wire could alternatively be used throughout, so long as those portions of the uninsulated flexile wire that are exposed on the contact-facing surface of the backing are insulated and shielded from electrical contact (step 94), such as by applying a layer of plastic, rubber-like polymers, or varnish, or by an additional layer of gauze or adhesive (or non-adhesive) gel over the exposed wire. The uninsulated flexile wire exposed on other surfaces of the backing could also be insulated or simply be left bare.

One end of the flexile wire may be terminated as an electrode signal pickup (step 95). If insulated flexile wire is used, a portion of the end of the flexile wire is stripped of insulation (step 96) using, for instance, a wire stripper or plasma jet. The electrode signal pickup could either be formed by interlacing (or sewing) the flexile wire (step 97) into the backing in the shape of the desired electrode (step 98) or positioned over the contact-facing area of the backing designated to serve as an electrode signal pickup and embedded within an electrically conductive adhesive (step 99). In a yet further embodiment, the flexile wire could be terminated as a connection to a discrete electrode, such as by sewing an uninsulated portion of the end of the electrode wire into the discrete electrode to thereby establish an electrical contact and affix the discrete electrode to the backing. The Universal ECG EKG electrode, manufactured by Bio Protech Inc., Tustin, Calif., is one example of a discrete electrode.

Finally, the other end of the flexile wire may be terminated as a connection to a circuit board (step 100). The flexile wire can be interlaced or sewn onto the circuit board, for instance, by back stitching the flexile wire back and forth across the edge of the circuit board to thereby establish an electrical contact and affix the discrete electrode to the backing.

In a further embodiment, flexile wire can be used to replace all or part of a printed circuit board, such as battery printed circuit board 62 used in constructing a stress-pliant physiological electrode assembly, as described supra, or for any other application that requires interconnection of electrical or electro mechanical components on a physical substrate or backing. Flexile wire in place of conductive circuit traces can work especially well with simple circuit board layouts, where ample space between components and relatively uncomplicated layouts are amenable to stitched-in interconnections. In addition, the use of flexile wire can simplify circuit layout design in multilayer circuits, as insulated flexile wires can be run across each other in situations that would otherwise require the use of a multilayer printed circuit board or similar solution.

Through such use of flexile wire, a printed circuit board can be omitted in whole or in part. Interconnects between and connections to the electronic and electro mechanical components formerly placed on the printed circuit board can instead be sewn from flexile wire. For instance, the battery printed circuit board 62 can be replaced by flexile wire interconnects that connect the electrodes to a sewn set of electrical pads formed by over-stitching the flexile wire into electrical contact surfaces of sufficient size to interface with a monitor recorder 14 when fitted into the non-conductive receptacle 25. Likewise, the spring 65 and clasp 66 can be sewn in place using flexile wire to hold a battery in place with flexile wire interconnects connecting the battery to a sewn set of electrical pads formed by over-stitching the flexile wire into electrical contact surfaces of sufficient size to interface with a monitor recorder 14 when fitted into the non-conductive receptacle 25. Still other approaches to replacing printed circuit boards with flexile wire interconnects are possible.

The resultant stress-pliant physiological electrode assembly may be electrically coupled to a broad range of physiological monitors not limited to electrocardiographic measurement. The foregoing method of constructing a stress-pliant electrode assembly is adaptable to manufacturing other forms of dermal electrodes, including electrodes for electrocardiography, electroencephalography, and skin conductance measurements. Further, by adjusting the number of electrodes, the distances among the electrode signal pickups, and the thickness of the flexile wire, the method can be adapted to manufacturing at low cost an electrode assembly that is lightweight and resistant to tensile, compressional and torsional forces, thus contributing to long-term wear and versatility.

While the invention has been particularly shown and described as referenced to the embodiments thereof, those skilled in the art will understand that the foregoing and other changes in form and detail may be made therein without departing from the spirit and scope.

What is claimed is:

1. An extended wear interlaced electrocardiography patch, comprising:
    a flexible backing formed of an elongated strip of stretchable material with narrow longitudinal midsection evenly tapering inward from a distal end and a proximal end, the elongated strip adherable only to a contact surface defined on each of the ends;
    a pair of flexile wires, one of the wires forming an electrocardiographic electrode, the electrocardiographic electrode formed by a portion of the one wire that is interlaced into the distal end of the elongated strip and that is configured for directly contacting a patient, the one wire continuing back along an axial path through the midsection, another one of the wires forming another electrocardiographic electrode, the electrocardiographic electrode formed by a portion of the another wire that is interlaced into the proximal end of the elongated strip and that is configured for electrically contacting the patient, each of the electrodes further comprising an electrically conductive area only exposed on the contact surface;
    a circuit board affixed on the proximal end of the elongated strip, comprising a battery compartment operable to hold a battery for powering an electrocardiography monitor, and one or more electrical pads operable to electrically couple the electrocardiography monitor with the pair of the electrodes; and
    a non-conductive receptacle securely adhered on one of the ends of the elongated strip opposite the contact surface and formed to removably receive the electrocardiography monitor.

2. An electrode patch according to claim 1, further comprising:
    one of the electrocardiographic electrodes being disposed for being adhered to a region overlying the lower sternum on the patient's chest; and
    an other of the electrocardiographic electrodes being disposed for being adhered to a region near the manubrium or upper sternum upwards on the patient's chest oriented centrally (in the midline) along the sternum from the one electrocardiographic electrode.

3. An electrode patch according to claim 1, further comprising:
    an upper part of the elongated strip defined on one end of the flexible backing and sized to be affixed to a bottom surface of the non-conductive receptacle, one of the electrocardiographic electrodes being affixed to and conductively exposed on the contact surface of the upper part; and
    a lower part of the elongated strip defined on another end of the flexible backing; another of the electrocardiographic electrodes being affixed to and conductively exposed on the contact surface of the lower part,
    wherein the lower part of the elongated strip is provided for being adhered to the region overlying the lower sternum on the patient's chest with the narrow longitudinal midsection oriented centrally (in the midline) along the sternum and the upper part of the elongated strip oriented upwards towards the manubrium.

4. An electrode patch according to claim 1, further comprising:
    a non-irritating adhesive dressing at least partially coated on each end of the elongated strip on the contact surface.

5. An electrode patch according to claim 1, further comprising:
    at least one pattern of interlaced flexile wires on the ends of the elongated strip selected from the group consisting of a circle, a square, and a triangle.

6. An electrode patch according to claim 1, further comprising:
    a plurality of holes arranged at regularly spaced intervals along an axial path defined between the circuit board and the distal end of the flexible backing, through which the one of the flexile wires is threaded.

7. An electrode patch according to claim 1, further comprising:
    a layer of insulation material covering at least part of a surface of the flexile wires.

8. An electrode patch according to claim 1, wherein the flexile wires comprise a metal selected from the group consisting of copper, aluminum, silver, and a combination thereof.

9. An electrode patch according to claim 1, wherein a form of a core of the flexile wires is selected from the group consisting of a solid, stranded, braided form, and a combination thereof.

10. An electrode patch according to claim 1, further comprising:
    the battery compartment provided in the non-conductive receptacle and comprising a pair of battery leads electrically coupleable to the battery; and the non-conductive receptacle further comprising power terminals aligned to electrically interface the pair of battery leads to the electrocardiography monitor.

11. An ambulatory electrocardiography interlaced electrode monitor, comprising:
   a disposable extended wear electrode patch, comprising:
      a flexible backing comprising stretchable material defined as an elongated strip with a narrow longitudinal midsection, each end of the flexible backing comprising an adhesive contact surface adapted to serve as a crimp relief;
      a pair of flexile wires, one of the wires forming an electrocardiographic electrode configured for directly contacting a patient, the electrocardiographic electrode formed by a portion of the one wire interlaced in a spiral pattern into a distal one of the ends of the elongated strip, the one wire interlaced along an axial path through the narrow longitudinal midsection to serve as a strain relief, another one of the wires forming another electrocardiographic electrode configured for directly contacting the patient, the another electrocardiographic electrode formed by a portion of the another wire interlaced in a further spiral pattern into a proximal one of the ends of the elongated strip, each electrocardiographic electrode conductively exposed for dermal adhesion and adapted to be positioned axially along a midline of a sternum of the patient;
      a non-conductive receptacle securely adhered on one of the ends of the elongated strip opposite the contact surface and formed to removably receive an ambulatory electrocardiography monitor recorder, the non-conductive receptacle comprising electrode terminals aligned to electrically interface the pair of the flexile wires to the ambulatory electrocardiography monitor recorder; and
   wherein the ambulatory electrocardiography interlaced electrode monitor further comprises the ambulatory electrocardiography monitor recorder, the ambulatory electrocardiography monitor recorder, comprising:
      a wearable housing adapted to securely fit into the non-conductive receptacle; and
      electronic circuitry provided within the wearable housing and comprising an external interface configured to be removably connected to the electrocardiographic electrodes via the non-conductive receptacle, further comprising:
         a microcontroller operable to execute over an extended period under micro programmable control as specified in firmware;
         an electrocardiographic front end circuit under the control of the microcontroller adapted to sense electrocardiographic signals through the electrocardiographic electrodes; and
         non-volatile memory electrically interfaced with the microcontroller and operable to continuously store samples of the electrocardiographic signals throughout the extended period.

12. An ambulatory electrocardiography interlaced electrode monitor according to claim 11, further comprising:
   one of the electrocardiographic electrodes being disposed for being adhered to a region overlying the lower sternum on the patient's chest; and
   an other of the electrocardiographic electrodes being disposed for being adhered to a region near the manubrium or upper sternum upwards on the patient's chest oriented centrally (in the midline) along the sternum from the one electrocardiographic electrode.

13. An ambulatory electrocardiography interlaced electrode monitor according to claim 11, further comprising:
   an upper part of the elongated strip defined on one end of the flexible backing and sized to be affixed to a bottom surface of the non-conductive receptacle, one of the electrocardiographic electrodes being affixed to and conductively exposed on the contact surface of the upper part; and
   a lower part of the elongated strip defined on another end of the flexible backing; another of the electrocardiographic electrodes being affixed to and conductively exposed on the contact surface of the lower part,
   wherein the lower part of the elongated strip is provided for being adhered to a region overlying the lower sternum on the patient's chest with the narrow longitudinal midsection oriented centrally (in the midline) along the sternum and the upper part of the elongated strip oriented upwards towards the manubrium.

14. An ambulatory electrocardiography interlaced electrode monitor according to claim 11, further comprising:
   a non-irritating adhesive dressing at least partially coated on each end of the elongated strip on the contact surface.

15. An ambulatory electrocardiography interlaced electrode monitor according to claim 11, wherein the spiral pattern and the further spiral pattern are the same.

16. An ambulatory electrocardiography interlaced electrode monitor according to claim 11, further comprising:
   a plurality of holes arranged at regularly spaced intervals along an axial path defined between the non-conductive receptacle and the distal end of the flexible backing, through which the one of the flexile wires is threaded.

17. An ambulatory electrocardiography interlaced electrode monitor according to claim 11, further comprising:
   a layer of insulation material covering at least part of a surface of the flexile wires.

18. An ambulatory electrocardiography interlaced electrode monitor according to claim 11, wherein the flexile wires comprise a metal selected from the group consisting of copper, aluminum, silver, and a combination thereof.

19. An ambulatory electrocardiography interlaced electrode monitor according to claim 11, wherein a form of a core of the flexile wires is selected from the group consisting of a solid, stranded, braided form, and a combination thereof.

20. An extended wear interlaced electrode electrocardiography patch, comprising:
   a flexible backing formed of an elongated strip of stretchable material with narrow longitudinal midsection evenly tapering inward from a distal end and a proximal end, the elongated strip adherable only to a contact surface defined on each of the ends;
   a pair of flexile wires, one of the wires forming an electrocardiographic electrode configured for directly contacting a patient, the electrocardiographic electrode formed by a portion of the one wire interlaced in a spiral pattern into the distal end of the elongated strip, the one wire continuing back along an axial path through the midsection, another one of the wires forming another electrocardiographic electrode, the electrocardiographic electrode formed by a portion of the another wire interlaced in a further spiral pattern into the proximal end of the elongated strip, each of the electrodes further comprising an electrically conductive area only exposed on the contact surface;

a circuit board affixed on the proximal end of the elongated strip, comprising a battery compartment operable to hold a battery for powering an electrocardiography monitor, and one or more electrical pads operable to electrically couple the electrocardiography monitor with the pair of the electrodes; and a non-conductive receptacle securely adhered on one of the ends of the elongated strip opposite the contact surface and formed to removably receive the electrocardiography monitor.

* * * * *